United States Patent
Coulter et al.

(10) Patent No.: US 11,179,344 B2
(45) Date of Patent: Nov. 23, 2021

(54) NANOPARTICLE-BASED LIVER-TARGETING THERAPY

(71) Applicant: Midatech Limited, Cardiff (GB)

(72) Inventors: Tom Coulter, Cardiff (GB); Philip Williams, Cardiff (GB)

(73) Assignee: Midatech Limited, Wales (GB)

( * ) Notice: Subject to any disclaimer, the term of this patent is extended or adjusted under 35 U.S.C. 154(b) by 202 days.

(21) Appl. No.: 16/473,620

(22) PCT Filed: Feb. 2, 2018

(86) PCT No.: PCT/EP2018/052716
§ 371 (c)(1),
(2) Date: Jun. 25, 2019

(87) PCT Pub. No.: WO2018/141940
PCT Pub. Date: Aug. 9, 2018

(65) Prior Publication Data
US 2021/0007997 A1    Jan. 14, 2021

(30) Foreign Application Priority Data
Feb. 2, 2017 (GB) .................................... 1701745

(51) Int. Cl.
| | |
|---|---|
| A61K 9/51 | (2006.01) |
| A61K 47/69 | (2017.01) |
| A61K 47/54 | (2017.01) |
| A61K 31/47 | (2006.01) |
| A61K 38/12 | (2006.01) |
| A61K 47/34 | (2017.01) |
| A61K 49/00 | (2006.01) |
| A61K 9/00 | (2006.01) |
| A61K 9/16 | (2006.01) |
| A61K 45/06 | (2006.01) |
| B82Y 5/00 | (2011.01) |

(52) U.S. Cl.
CPC ............ *A61K 9/5115* (2013.01); *A61K 31/47* (2013.01); *A61K 38/12* (2013.01); *A61K 47/34* (2013.01); *A61K 47/549* (2017.08); *A61K 47/6923* (2017.08); *A61K 47/6929* (2017.08); *A61K 49/0041* (2013.01); *A61K 49/0093* (2013.01); *A61K 9/0019* (2013.01); *A61K 9/1647* (2013.01); *A61K 45/06* (2013.01); *B82Y 5/00* (2013.01)

(58) Field of Classification Search
CPC .............. A61K 9/5115; A61K 47/6929; A61K 47/6923; A61K 47/549; A61K 31/47; A61K 38/12; A61K 47/34; A61K 49/0041; A61K 49/0093; A61K 9/0019; A61K 9/1647; A61K 45/06; B82Y 5/00
See application file for complete search history.

(56) References Cited

FOREIGN PATENT DOCUMENTS

| | | |
|---|---|---|
| WO | 2016/075211 | 5/2016 |
| WO | 2017/017063 | 2/2017 |
| WO | 2017/144551 | 8/2017 |

OTHER PUBLICATIONS

Christian K. Adokoh et al.; (2014) "Synthesis and Evaluation of Glycopolymeric Decorated Gold Nanoparticles Functionalized with Gold-Triphenyl Phosphine as Anti-Cancer Agents", Biomacromolecules, 15(10):3802-3810.
Seema Garg et al.; (2013) "Synthesis of a Smart Gold Nano-vehicle for Liver Specific Drug Delivery", AAPS Pharmscitech, 14(3)1219-12.

*Primary Examiner* — Robert S Cabral
(74) *Attorney, Agent, or Firm* — Carol L. Francis; Rudy J. Ng; Bozicevic, Field & Francis LLP

(57) ABSTRACT

The present invention provides a nanoparticle comprising: a core comprising a metal and/or a semiconductor; and a plurality of ligands covalently linked to the core, wherein said ligands comprise: at least one liver-targeting ligand, such as C2-alpha galactose; at least one payload ligand comprising a bioactive agent, such as maytansinoid DM1; and at least one dilution ligand comprising a poly(ethyleneglycol) (PEG) moiety, such as PEG COOH. Also provided are pharmaceutical compositions comprising the nanoparticle, and uses of the nanoparticle in methods of treatment of liver disorders, including liver cancers such as hepatocellular carcinoma (HCC).

21 Claims, 16 Drawing Sheets
Specification includes a Sequence Listing.

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: glypican-3 binding peptide

<400> SEQUENCE: 1

Arg Leu Asn Val Gly Gly Thr Tyr Phe Leu Thr Thr Arg Gln
1               5                   10

<210> SEQ ID NO 2
<211> LENGTH: 7
<212> TYPE: PRT
<213> ORGANISM: Artificial Sequence
<220> FEATURE:
<223> OTHER INFORMATION: glypican-3 binding peptide

<400> SEQUENCE: 2

Tyr Phe Leu Thr Thr Arg Gln
1               5
```

NANOPARTICLE-BASED LIVER-TARGETING THERAPY

This application claims priority from GB Application No. 1701745.0 filed 2 Feb. 2017, the contents and elements of which are herein incorporated by reference for all purposes.

FIELD OF THE INVENTION

The present invention relates to nanoparticles as vehicles for the targeted delivery of agents to specific tissue types or locations, particularly for use in medicine, and includes methods for treatment of liver disorders such as liver cancer. Pharmaceutical compositions, processes for production of the nanoparticles and methods for their use are also disclosed.

BACKGROUND TO THE INVENTION

The present invention is directed at compositions and products, and methods of making and administering such compositions and products, including for the treatment of mammals and particularly humans.

Drug delivery poses several significant challenges, particularly with regard to the site of action. In the case of treatment of certain tumours, for example, there remains a need for delivery systems that are able to target anti-cancer drugs to the tumour site, while minimizing off-target effects.

Primary liver cancer is the sixth most frequent cancer globally and the second leading cause of cancer death. The most frequent liver cancer, accounting for approximately 75% of all primary liver cancers, is hepatocellular carcinoma (HCC). HCC is formed by hepatocytes that become malignant. Hepatitis B, Hepatitis C, aflatoxin B1 and the abuse of alcohol are the four agents responsible for approximately 80% of the human HCCs. Hence, underlying diseases like steatohepatitis, fibrosis and cirrhosis often complicate conventional HCC therapy. Currently, surgical resection is the major treatment option for HCC if the tumour is resectable. However, only 10-20% of HCC can be removed completely using surgery. Therefore, targeted drug delivery is of crucial interest due to both improvement of efficacy of approved chemotherapeutics and reducing their side effects (Shi B. et al., *J. Histochem. Cytochem.*, 2013, Vol. 61, pp. 901-909).

WO0232404 describes carbohydrate-coupled (including lactose-coupled) gold nanoparticles. WO2014/125256 describes nanoparticle delivery systems for use in targeting biologically active agents to the central nervous system (CNS), e.g., for treatment of CNS disorders.

Garg et al., *AAPS PharmSciTech*, 2013, Vol. 14, No. 3, pp. 1219-1226, describes a lactose surface-modified gold nanovehicle for the intracellular delivery of a fluorescent coumarin derivative to hepatic cells.

Penadés et al., *Chem. Eur. J.*, Vol. 9, pp. 1909-1921 describes the synthesis of fluorescent glyconanoparticles.

Penadés et al., *Carbohydrate Research*, Vol. 344, pp. 1474-1478 describes studies evaluating the influence of ligand density and presentation on the recognition of protein receptors using lactose-functionalised gold nanoparticles.

Penadés et al., *Chem. Bio. Chem.*, Vol. 5, pp. 291-297 describes studies investigating the use of glyconanoparticles presenting lactose to reduce the progress of experimental metastasis.

WO 2017/017063 and GB2541166 describe nanoparticle-based liver-targeting therapy and imaging.

There remains an unmet need for further nanoparticle delivery systems and for methods of delivering bioactive and/or detectable agents to a specific tissue or location in a subject, including for the targeted treatment of primary liver cancer. The present invention addresses these and other needs.

BRIEF DESCRIPTION OF THE INVENTION

Broadly, the present invention relates to nanoparticles provided with a liver-targeting moiety and a payload, which nanoparticles are useful as vehicles for the delivery of the payload to the liver, including to diseased cells of the liver. The payload may comprise one or more bioactive agents for therapeutic applications.

In a first aspect the present invention provides nanoparticle comprising:
  a core comprising a metal and/or a semiconductor; and
  a plurality of ligands covalently linked to the core, wherein said ligands comprise:
    (i) at least one liver-targeting ligand;
    (ii) at least one payload ligand comprising a bioactive agent; and
    (iii) at least one dilution ligand comprising a polyethyleneglycol (PEG) moiety.

As described in detail herein, a [DM1]-[C2-α-Galactose]-[PEG8COOH]@Au nanoparticle according to the present invention has been found to enable otherwise lethal doses of DM1 to be administered, facilitates greater tumour delivery (i.e. higher tumour DM1 concentration vs. delivery of free DM1), improved animal survival and exhibited a six-fold greater reduction in in vivo tumour growth compared to the current standard of care (SoC), Sorafenib.

In some cases, the liver-targeting ligand comprises galactose, such as alpha-galactose.

The liver-targeting ligand is covalently linked to the core via a first linker, said first linker having a chain length of 2 to 50 atoms. In some cases, the first linker comprises a group —(CH$_2$)$_n$— and/or —(OCH$_2$CH$_2$)$_m$—, wherein n and m are independently ≥1.

The first linker may be bound to the core via a terminal sulphur atom.

In some cases, the at least one payload ligand comprises a therapeutic agent. In particular, the therapeutic agent may be a chemotherapeutic or cytotoxic compound.

In certain cases the payload ligand comprises a compound selected from the group consisting of: maytansinoid DM1, maytansinoid DM4, doxorubicin, irinotecan, Platinum (II), Platinum (IV), temozolomide, carmustine, camptothecin, docetaxel, sorafenib, maytansine, monomethyl auristatin E (MMAE) and panobinostat.

In some cases, the at least one dilution ligand comprises a poly or oligo ethylene glycol chain. The dilution ligand may comprise a negatively charged end group or an end group capable of having negative charge at physiological pH. The dilution ligand may have a carboxylic acid end group. In particular, the dilution ligand may comprise SH-PEG-COOH. In certain cases, the at least one dilution ligand comprises: HS—(OCH$_2$CH$_2$)$_q$—COOH, where q is between 2 and 30, optionally between 6 and 10. In certain cases q may be 2, 3, 4, 5, 6, 7, 8, 9, 10, 11, 12, 13, 14, 15, 16, 17, 18, 19 or 20. In certain cases, one or more ligands having longer PEG chains may be employed alone or in combination with ligands having shorter PEG chains. Preliminary data suggest that a nanoparticle of the invention having ligands of PEG2000 (i.e. poly(ethylene glycol) having a molecular weight in the range 1900 to 2200) exhibits a longer half-life (t$_{1/2}$) in comparison with a nanoparticle of the invention having a shorter PEG chain. Accordingly, in some embodiments, the dilution ligand may comprise a poly(ethylene glycol) moiety, linear or branched having an average molecular weight in the range 1000 to 3000 Daltons, for example 1900 to 2200. In particular embodiments, the dilution ligand may comprise HS—(OCH$_2$CH$_2$)$_q$—COOH, wherein q is chosen so as to provide an average molecular weight in the range 1000 to 3000 Daltons, such as 1900 to 2200 Daltons. In certain cases, q may be in the range 20 to 60, such as 40 to 50. In certain cases the number of longer PEG ligands may in around 1 to 10, e.g. 1 to 8, per nanoparticle core. It is specifically contemplated that the nanoparticle may comprise both a plurality of (e.g. 10-50) shorter PEG-containing ligands (e.g. HS—(OCH$_2$CH$_2$)$_q$—COOH, where q is between 2 and 30, optionally between 6 and 10) and one or more (e.g. 1-10) longer PEG-containing ligands (e.g. HS—(OCH$_2$CH$_2$)$_p$—COOH, wherein p in the range 20 to 60, optionally 40 to 50).

In certain embodiments, the at least one dilution ligand comprises:

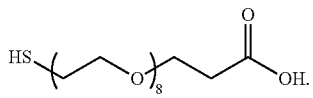

In some cases the plurality of ligands comprise:
at least one galactose ligand;
at least one maytansinoid DM1 ligand; and
at least one dilution ligand comprising SH-PEG-COOH.
In some cases, SH-PEG-COOH is SH-PEG$_8$-COOH.

In some cases the plurality of ligands comprise:
at least one galactose ligand (e.g. SH—C$_2$H$_2$-alpha-galactose);
at least one maytansinoid DM1 ligand, for example 3 to 8 maytansinoid DM1 ligands per core or 4 to 6 maytansinoid DM1 ligands per core or around 5 maytansinoid DM1 ligands per core; and
at least one dilution ligand comprising SH-PEG-COOH. In some cases, SH-PEG-COOH is SH-PEG$_8$-COOH, i.e. 1-Mercapto-3,6,9,12,15,18,21,24-octaoxaheptacosan-27-oic acid.

In some cases the plurality of ligands comprise only (i.e. there are no other species of ligands covalently linked to the nanoparticle core):
at least one galactose ligand (e.g. SH—C$_2$H$_2$-alpha-galactose);
at least one maytansinoid DM1 ligand, for example 3 to 8 maytansinoid DM1 ligands per core or 4 to 6 maytansinoid DM1 ligands per core or around 5 maytansinoid DM1 ligands per core; and
at least one dilution ligand comprising SH-PEG-COOH. In some cases, SH-PEG-COOH is SH-PEG$_8$-COOH, i.e. 1-Mercapto-3,6,9,12,15,18,21,24-octaoxaheptacosan-27-oic acid.

In some cases, the core comprises a metal selected from the group consisting of: Au, Ag, Cu, Pt, Pd, Fe, Co, Gd, Zn or any combination thereof. In particular, the core may be of gold.

In some cases, the diameter of the core is in the range 1 nm to 5 nm, for example in the range 2 nm to 4 nm.

In some cases, the diameter of the nanoparticle including its ligands is in the range 3 nm to 50 nm.

In some cases, the nanoparticle of this aspect of the invention has the following general structure:

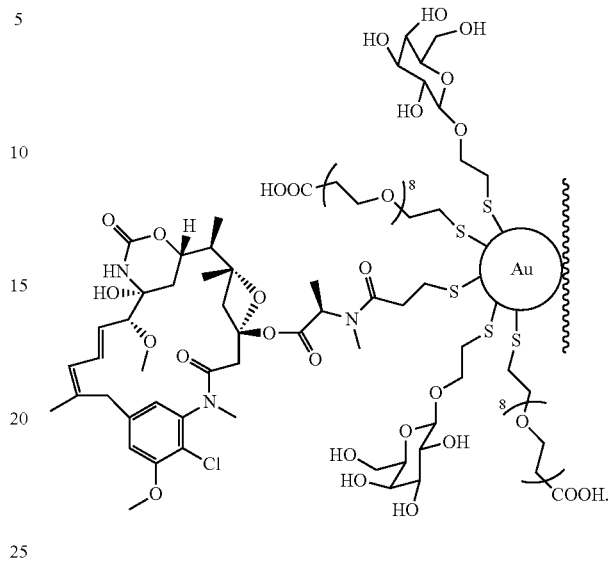

The number of maytansinoid DM1 ligands may, for example, be in the range 3 to 8 per nanoparticle core, such as 4 to 6 per core or around 5 maytansinoid DM1 ligands per core. The number of alpha-galactose-containing ligands and/or PEG$_8$COOH-containing ligands will typically be higher, such as more than 10 or more than 20. In some cases, the number of alpha-galactose-containing ligands and/or PEG$_8$COOH-containing ligands will be not more than 50, such as not more than 25 or even not more than 20 per core. In particular embodiments, the ligands may be in the following proportions (which may be determined, e.g., by NMR and/or by input proportion during synthesis):
Alpha-Galactose 45-50%/17-20 per core;
PEG8-COOH 45-50%/17-20 per core; and
DM1 10-15%/4.5-6 per core.

In a second aspect, the present invention provides a pharmaceutical composition comprising a plurality of nanoparticles of the first aspect of the invention and at least one pharmaceutically acceptable carrier or diluent.

The pharmaceutical composition may be a sustained release formulation, wherein at least a portion of the plurality of nanoparticles are encapsulated in a biocompatible polymer. The sustained release formulation may be in the form of a microparticle, a microsphere, a bead or a film.

In some cases the pharmaceutical composition of the second aspect of the invention is in injectable form.

In a third aspect the present invention provides a nanoparticle of the first aspect of the invention or a pharmaceutical composition of the second aspect of the invention for use in medicine.

In a fourth aspect the present invention provides a nanoparticle of the first aspect of the invention or a pharmaceutical composition of the second aspect of the invention for use in the treatment of a liver disorder in a mammalian subject.

In some cases the liver disorder comprises a primary or secondary cancer of the liver.

In particular, the cancer may be hepatocellular carcinoma (HCC). In certain cases, the HCC may be advanced stage C or intermediate stage B according to the Barcelona classification (see, e.g., Llovet et al., 2004, *Liver Transplantation*, Vol. 10, No. 2, Suppl. 1, pp. S115-S120). In certain cases, the HCC may have been determined to be unsuitable for surgical resection.

In certain cases, the cancer may be selected from: heptoblastoma, cholangiocarcinoma, cholangiocellular cystadenocarcinoma, angiosarcoma, hemangioendothelioma, embryonal sarcoma, fibrosarcoma, leiomyosarcoma and rhabdomyosarcoma.

In certain cases in accordance with the fourth aspect the present invention, the nanoparticle of the first aspect of the invention or a pharmaceutical composition of the second aspect of the invention may be for use in a method treatment of said liver disorder (e.g. a liver cancer such as HCC) in a mammalian subject in which said nanoparticle or said pharmaceutical composition is administered concurrently, sequentially or separately with a second anti-cancer agent. In particular cases, said second anti-cancer agent may comprise a kinase inhibitor (e.g. protein tyrosine kinase inhibitor), such as Sorafenib (NEXAVAR®), Regorafenib (STIVARGA®), and/or Lenvatinib (LENVIMA®). In particular cases, said second anti-cancer agent may comprise a monoclonal antibody, such as an anti-PD-1 monoclonal antibody (e.g. Nivolumab (OPDIVO®)), an anti-CTLA4 monoclonal antibody (e.g. ipilumumab (Yervoy®)), and anti-PD-L1 monoclonal antibody (e.g. atezolizumab (Tecentriq®), an antibody that binds CD223, an antibody that binds TIM-3, or an antibody that binds OX-40. Combination therapy employing a nanoparticle of the present invention or pharmaceutical composition comprising the nanoparticle together (e.g. sequential administration) with a second anti-cancer agent, such as Sorafenib, may exhibit superior clinical efficacy in comparison to either agent administered alone. It is contemplated that the combination therapy may comprise intraveneous administration of a pharmaceutical composition comprising the nanoparticle of the present invention and oral administration of a second anti-cancer agent, such as a kinase inhibitor as mentioned above.

In certain cases, the method treatment of said liver disorder (e.g. a liver cancer such as HCC) in a mammalian subject may comprise administering said nanoparticle or said pharmaceutical composition in combination with transarterial chemoembolization (TACE) therapy.

In a fifth aspect the present invention provides a method of treating a liver disorder in a mammalian subject, comprising administering a nanoparticle of the first aspect of the invention or a pharmaceutical composition of the second aspect of the invention to the subject in need of therapy.

In some cases the liver disorder comprises a primary or secondary cancer of the liver.

In particular, the cancer may be hepatocellular carcinoma (HCC).

In certain cases, the cancer may be selected from: heptoblastoma, cholangiocarcinoma, cholangiocellular cystadenocarcinoma, angiosarcoma, hemangioendothelioma, embryonal sarcoma, fibrosarcoma, leiomyosarcoma and rhabdomyosarcoma.

In certain cases in accordance with the fifth aspect the present invention, the method treatment of said liver disorder (e.g. a liver cancer such as HCC) may comprise administering said nanoparticle or said pharmaceutical composition concurrently, sequentially or separately with a second anti-cancer agent. In particular cases, said second anti-cancer agent may comprise a kinase inhibitor (e.g. protein tyrosine kinase inhibitor), such as Sorafenib (NEXAVAR®), Regorafenib (STIVARGA®), and/or Lenvatinib (LENVIMA®), In particular cases, said second anti-cancer agent may comprise a monoclonal antibody, such as an anti-PD-1 monoclonal antibody (e.g. Nivolumab (OPDIVO®)), an anti-CTLA4 monoclonal antibody (e.g. ipilumumab (Yervoy®)), and anti-PD-L1 monoclonal antibody (e.g. atezolizumab (Tecentriq®), an antibody that binds CD223, an antibody that binds TIM-3, or an antibody that binds OX-40. Combination therapy employing a nanoparticle of the present invention or pharmaceutical composition comprising the nanoparticle together (e.g. sequential administration) with a second anti-cancer agent, such as Sorafenib, may exhibit superior clinical efficacy in comparison to either agent administered alone. It is contemplated that the combination therapy may comprise intraveneous administration of a pharmaceutical composition comprising the nanoparticle of the present invention and oral administration of a second anti-cancer agent, such as a kinase inhibitor as mentioned above.

In certain cases, the method treatment of said liver disorder (e.g. a liver cancer such as HCC) in a mammalian subject may comprise administering said nanoparticle or said pharmaceutical composition in combination with transarterial chemoembolization (TACE) therapy.

In a sixth aspect the present invention provides use of a nanoparticle of the first aspect of the invention or a pharmaceutical composition of the second aspect of the invention in the preparation of a medicament for use in a method of the fifth aspect of the invention.

In a seventh aspect the present invention provides an article of manufacture comprising:
- a nanoparticle of the first aspect of the invention or a pharmaceutical composition of the second aspect of the invention;
- a container for housing the nanoparticle or pharmaceutical composition; and
- an insert or label.

In some cases the insert and/or label provides instructions, dosage and/or administration information relating to the use of the nanoparticle or pharmaceutical composition in the treatment of a liver disorder in a mammalian subject.

The present invention includes the combination of the aspects and preferred features described except where such a combination is clearly impermissible or is stated to be expressly avoided. These and further aspects and embodiments of the invention are described in further detail below and with reference to the accompanying examples and figures.

DETAILED DESCRIPTION OF THE INVENTION

Figure 1:
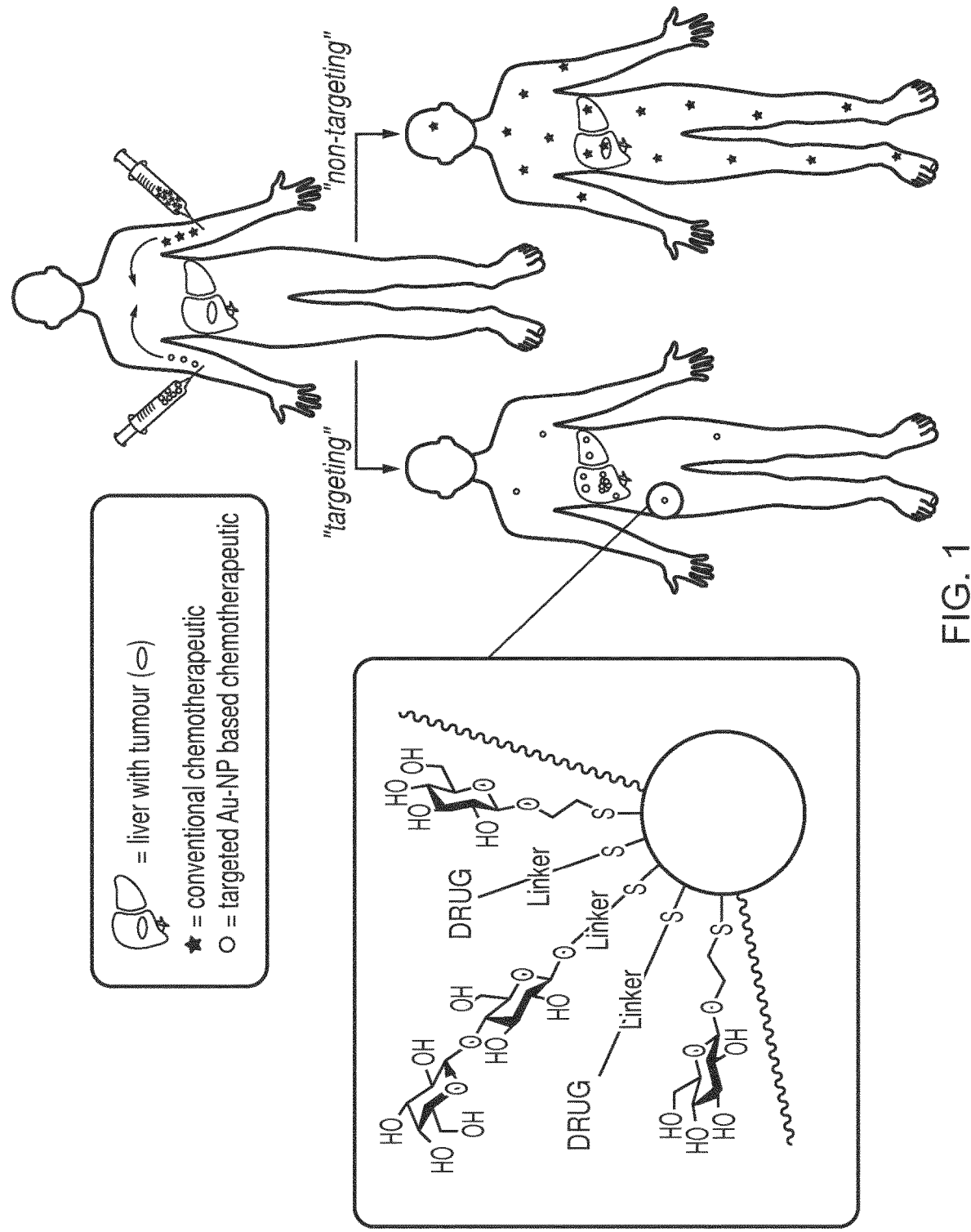
FIG. 1 shows a schematic and simplified depiction of biodistribution for conventional chemotherapeutics and liver-targeted nanoparticles.

In describing the present invention, the following terms will be employed, and are intended to be defined as indicated below.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

Liver-Targeting Ligands

The liver-targeting ligand binds, couples to or interacts with a receptor, marker, protein or antigen present at, in or on liver cells (in some cases healthy liver cells, in other cases only or predominantly cancer cells of a liver tumour, e.g. hepatocellular carcinoma, in yet other cases present at, in or on both healthy liver cells and cancer cells of a liver tumour). In binding or otherwise being attracted to the liver (or a tumour thereof), the liver-targeting ligand assists with targeting the nanoparticle of the invention to the site of intended action. The liver-targeting ligand is covalently linked to the nanoparticle core (directly or more commonly via a linker) and therefore acts to cause the nanoparticle, including its payload, to associate with or otherwise come into contact with the liver (or a tumour thereof) with greater frequency, for longer duration and/or at higher concentration than would be the case for the nanoparticle in the absence of the liver-targeting ligand. As used herein the term "liver-targeting ligand" specifically includes not only ligands that actively target the liver, but also includes ligands that passively target the liver and/or which aid passive uptake by liver cells and/or liver cancer cells.

Examples of liver-targeting ligands include: galactose (e.g. alpha-galactose), lactose, FGF-4 (fibroblast growth factor 4), c-Met (hepatocyte growth factor receptor), a glypican-3 binding agent (e.g. a glypican-3 binding peptide as disclosed in U.S. Pat. No. 8,388,937 (including specifically the peptides of SEQ ID NOs: 1, 2, 3, 4, 5, 6, 7 and 10 therein, which are expressly incorporated herein by reference) or an anti-glypican-3 antibody), an alpha-fetoprotein (AFP) receptor binding agent (e.g. an AFP receptor binding peptide as disclosed in US2012/0270238 or an anti-AFP receptor antibody), and an ASGPR binding agent (e.g. galactose, N-acetylgalactosamine, lactose, glucose, mannose, or a glycomimetic ligand such as disclosed in Mamidyala et al., *J. Am. Chem. Soc.*, 2012, Vol. 1334, No. 4, pp. 1978-1981). The liver-targeting ligand may also be an antibody or binding fragment thereof, e.g. a Fab fragment (fragment antigen-binding), single domain antibody/nanobody directed at a liver or hepatocyte target such as glypican-3, ASGPR, FGF-4, c-Met, AFP or other liver-expressed protein or liver-expressed receptor.

Figure 2:
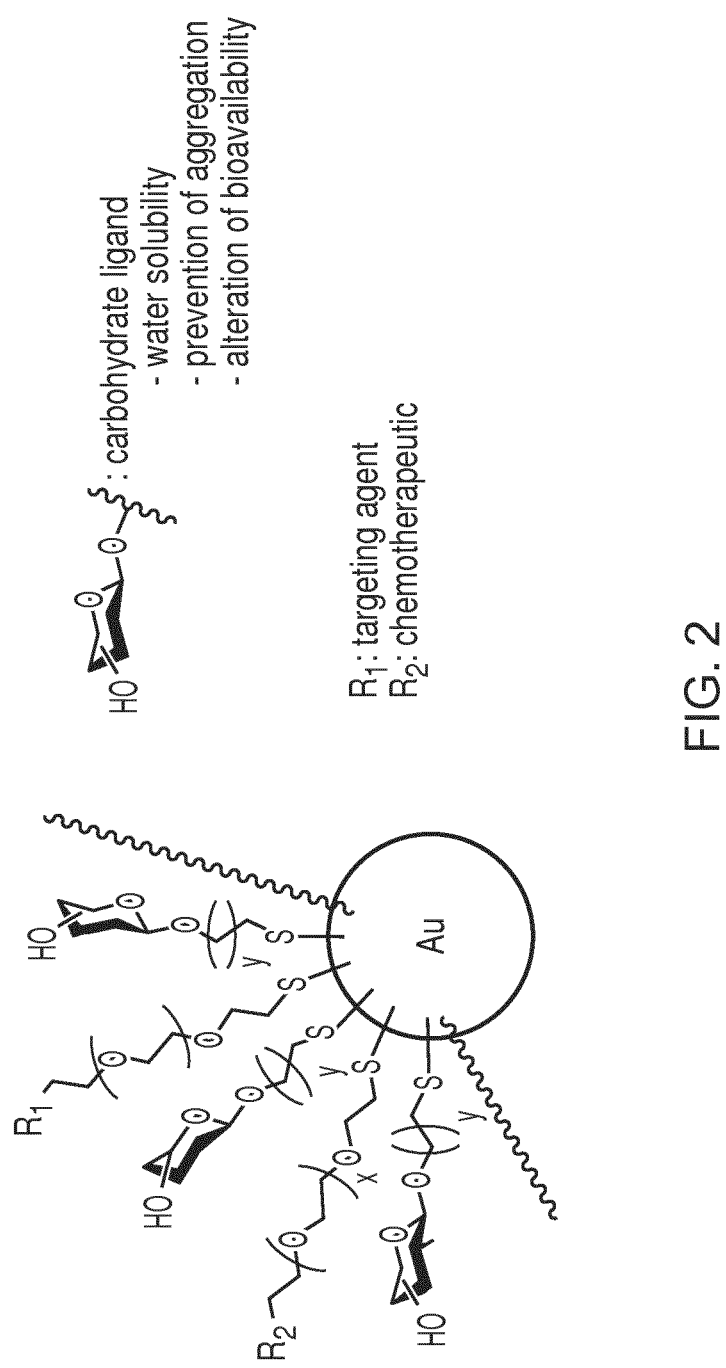
FIG. 2 shows a schematic depiction of a functionalised gold nanoparticle with carbohydrate (dilution) ligands, targeting agent ($R_1$) containing ligands and chemotherapeutic ($R_2$) containing ligands. Repeating ethylene glycol and alkyl groups are indicated by the subscripts x and y, respectively.

The asialoglycoprotein receptor (ASGPR) is believed to be a suitable target for targeting payload-carrying nanoparticles to the liver. ASGPR recognises galactose residues and is expressed in the liver and not in other human tissues. The combined attachment of targeting agents (such as lactose) and chemotherapeutic to an ultra-small glyco-coated gold nanoparticle (1.6-1.8 nm) provides unique properties for the treatment of HCC. After administration and circulation in the body the targeted Au-NPs accumulate in the liver and ASPGR overexpressing HCC (FIG. 1, "targeting"), whereas a conventional chemotherapeutic is widely distributed (FIG. 1, "non-targeting"). Furthermore, the small Au-NPs (<2 nm) show increased tumour penetration potential compared to larger NPs (~15 nm) and provide a beneficial surface coverage (Huang, K. et al., *ACS Nano,* 2012, Vol. 6, pp. 4483-4493; Kumara, C. et al., *ACS Nano,* 2014, Vol. 8, pp. 6431-6439). A schematic of such a functionalised gold nanoparticle is shown in FIG. 2.

The ligand corona exhibits meta stability under physiological conditions due to the Au-sulphur bond, stable in plasma and released in the cytosol. Here, we present promising results of a targeted GNP chemotherapeutic screening study utilising in vitro, ex vivo and in vivo model towards efficient liver targeting.

Glypican-3 binding peptides include RLNVGGTYFLT-TRQ (SEQ ID NO: 1), YFLTTRQ (SEQ ID NO: 2) and variants thereof differing from said sequence by addition, deletion, substitution or chemical modification (e.g. unnatural or modified amino acids) of not more than 3, not more than 2 or not more than 1 amino acid. Said variants may for example comprise one, two or three unnatural or modified amino acids. Suitable unnatural amino acids include, for example, D-amino acids, ornithine, diaminobutyric acid ornithine, norleucine ornithine, pyriylalanine, thienylalanine, naphthylalanine, phenylglycine, alpha and alpha-disubstituted amino acids, N-alkyl amino acids, lactic acid, halide derivatives of natural amino acids, such as trifluorotyrosine, p-Cl-phenylalanine, p-Br-phenylalanine, p-I-phenylalanine, L-allyl-glycine, b-alanine, L-a-amino butyric acid, L-g-amino butyric acid, L-a-amino isobutyric acid, L-e-amino caproic acid, 7-amino heptanoic acid, L methionine sulfone, L-norleucine, L-norvaline, p-nitro-L-phenylalanine, L-hydroxyproline, L-thioproline, methyl derivatives of phenylalanine—such as 1-methyl-Phe, pentamethyl-Phe, L-Phe(4-amino), L-Tyr(methyl), L-Phe(4-isopropyl), L-Tic(1,2,3,4-tetrahydroisoquinoline-3-carboxyl acid), L-diaminopropionic acid and L-Phe(4-benzyl). The peptides may be further modified. For example, one or more amide bonds may be replaced by ester or alkyl backbone bonds. There may be N or C alkyl substituents, side chain modifications or constraints such as disulphide bridges, side chain amide or ester linkages. The variant peptides may include both modified peptides and synthetic peptide analogues. Peptides may be, for example, be modified to improve solubility, formulation and storage properties, or to protect labile peptide bonds by incorporating non-peptidic structures.

It is specifically contemplated herein that the N-terminus and/or C-terminus of a peptide, such as a glypican-3 binding peptide, may be modified by N-terminal acetylation and/or C-terminal amidation. In particular, such terminal modification(s) may assist with the covalent attachment of the liver-targeting peptide to the nanoparticle (e.g. via a linker).

Nanoparticles

As used herein, "nanoparticle" refers to a particle having a nanomeric scale, and is not intended to convey any specific shape limitation. In particular, "nanoparticle" encompasses nanospheres, nanotubes, nanoboxes, nanoclusters, nanorods and the like. In certain embodiments the nanoparticles and/or nanoparticle cores contemplated herein have a generally polyhedral or spherical geometry. References to "diameter" of a nanoparticle or a nanoparticle core a generally taken to mean the longest dimension of the nanoparticle or nanoparticle core, respectively. For nanoparticles having a substantially polyhedral or spherical geometry, the shortest dimension across the particle will typically be within 50% of the longest dimension across the particle and may be, e.g., within 25% or 10%.

Nanoparticles comprising a plurality of carbohydrate-containing ligands have been described in, for example, WO 2002/032404, WO 2004/108165, WO 2005/116226, WO 2006/037979, WO 2007/015105, WO 2007/122388, WO 2005/091704 (the entire contents of each of which is expressly incorporated herein by reference) and such nanoparticles may find use in accordance with the present invention.

As used herein, "corona" refers to a layer or coating, which may partially or completely cover the exposed surface of the nanoparticle core. The corona includes a plurality of ligands covalently attached to the core of the nanoparticle. Thus, the corona may be considered to be an organic layer that surrounds or partially surrounds the metallic core. In certain embodiments the corona provides and/or participates in passivating the core of the nanoparticle. Thus, in certain cases the corona may include a sufficiently complete coating layer substantially to stabilise the core. In certain cases the corona facilitates solubility, such as water solubility, of the nanoparticles of the present invention.

Nanoparticles are small particles, e.g. clusters of metal or semiconductor atoms, that can be used as a substrate for immobilising ligands.

Preferably, the nanoparticles have cores having mean diameters between 0.5 and 50 nm, more preferably between 0.5 and 10 nm, more preferably between 0.5 and 5 nm, more preferably between 0.5 and 3 nm and still more preferably between 0.5 and 2.5 nm. When the ligands are considered in addition to the cores, preferably the overall mean diameter of the particles is between 2.0 and 50 nm, more preferably between 3 and 10 nm and most preferably between 4 and 5 nm. The mean diameter can be measured using techniques well known in the art such as transmission electron microscopy.

The core material can be a metal or semiconductor and may be formed of more than one type of atom. Preferably, the core material is a metal selected from Au, Fe or Cu. Nanoparticle cores may also be formed from alloys including Au/Fe, Au/Cu, Au/Gd, Au/Fe/Cu, Au/Fe/Gd and Au/Fe/Cu/Gd, and may be used in the present invention. Preferred core materials are Au and Fe, with the most preferred material being Au. The cores of the nanoparticles preferably comprise between about 100 and 500 atoms (e.g. gold atoms) to provide core diameters in the nanometre range. Other particularly useful core materials are doped with one or more atoms that are NMR active, allowing the nanoparticles to be detected using NMR, both in vitro and in vivo. Examples of NMR active atoms include $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$, or the quantum dots.

Nanoparticle cores comprising semiconductor compounds can be detected as nanometre scale semiconductor crystals are capable of acting as quantum dots, that is they can absorb light thereby exciting electrons in the materials to higher energy levels, subsequently releasing photons of light at frequencies characteristic of the material. An example of a semiconductor core material is cadmium selenide, cadmium sulphide, cadmium tellurium. Also included are the zinc compounds such as zinc sulphide.

In some embodiments, the nanoparticle or its ligand comprises a detectable label. The label may be an element of the core of the nanoparticle or the ligand. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamines or tetramethyl rhodamine, Texas-Red, Cy3, Cy5, etc., and may be detected by excitation of the fluorescent label and detection of the emitted light using Raman scattering spectroscopy (Y.C. Cao, R. Jin, C. A. Mirkin, Science 2002, 297: 1536-1539).

In some embodiments, the nanoparticles may comprise a radionuclide for use in detecting the nanoparticle using the radioactivity emitted by the radionuclide, e.g. by using PET, SPECT, or for therapy, i.e. for killing target cells. Examples of radionuclides commonly used in the art that could be readily adapted for use in the present invention include $^{99m}Tc$, which exists in a variety of oxidation states although the most stable is $TcO^{4-}$; $^{32}P$ or $^{33}P$; $^{57}Co$; $^{59}Fe$; $^{67}Cu$ which is often used as $Cu^{2+}$ salts; $^{67}Ga$ which is commonly used a $Ga^{3+}$ salt, e.g. gallium citrate; $^{68}Ge$; $^{82}Sr$; $^{99}Mo$; $^{103}Pd$; $^{111}In$ which is generally used as $In^{3+}$ salts; $^{125}I$ or $^{131}I$ which is generally used as sodium iodide; $^{137}Cs$; $^{153}Gd$; $^{153}Sm$; $^{158}Au$; $^{186}Re$; $^{201}Tl$ generally used as a $Tl^+$ salt such as thallium chloride; $^{39}Y^{3+}$; $^{71}Lu^{3+}$; and $^{24}Cr^{2+}$. The general use of radionuclides as labels and tracers is well known in the art and could readily be adapted by the skilled person for use in the aspects of the present invention. The radionuclides may be employed most easily by doping the cores of the nanoparticles or including them as labels present as part of ligands immobilised on the nanoparticles.

Actives

As used herein the term "biologically active agent" or "bioactive agent" is intended to encompass drugs and pro-drugs that exert an effect on a biological system, preferably a therapeutic effect. Class of active agent contemplated herein include small molecule organic compounds, peptides, polypeptides and nucleic acids. An exemplary class of therapeutic agent is an anti-cancer agent, such as a cytotoxic compound, an anti-proliferative agent or an anti-angiogenic agent. Particular examples include chemotherapeutic agents, e.g. a maytansinoid (e.g. maytansinoid DM1 or maytansinoid DM4), doxorubicin, temozolomide, irinotecan, carmustine, platinum(IV), platinum(II), camptothecin, docetaxel, sorafenib, maytansine, monomethyl auristatin E (MMAE) and a histone deacetylase (HDAC) inhibitor (e.g. panobinostat).

In certain cases, the at least one payload ligand is selected from:
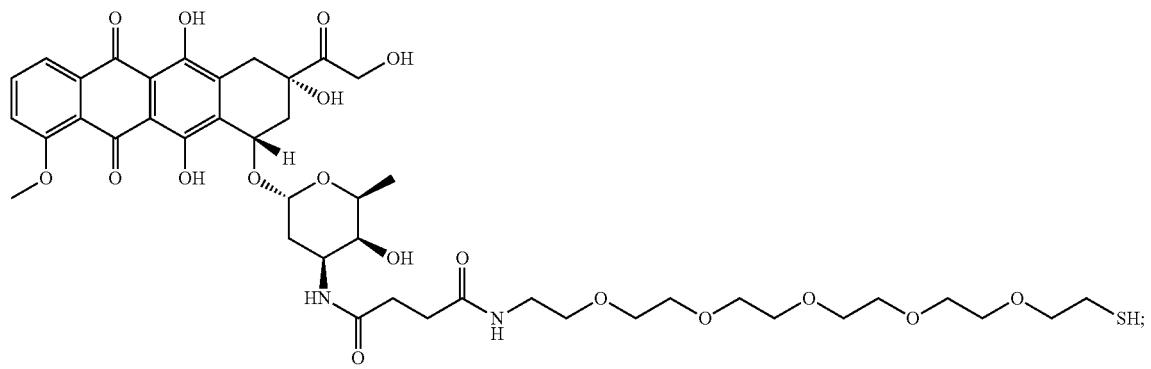
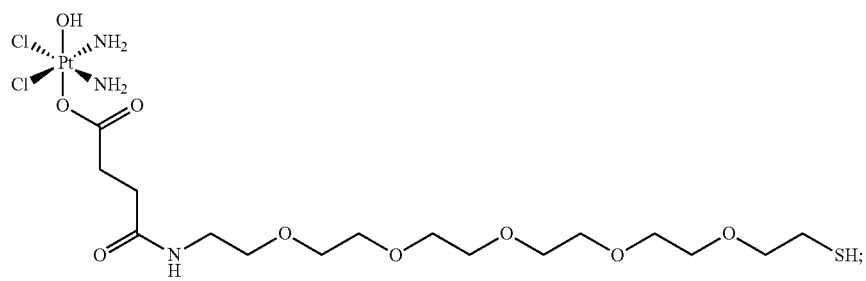
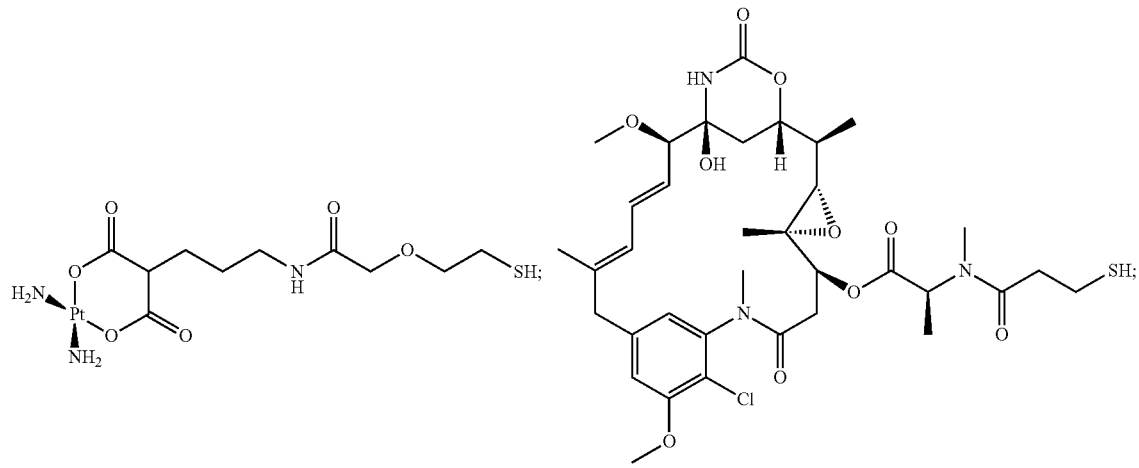
(Maytansinoid DM1, "Mertansine")
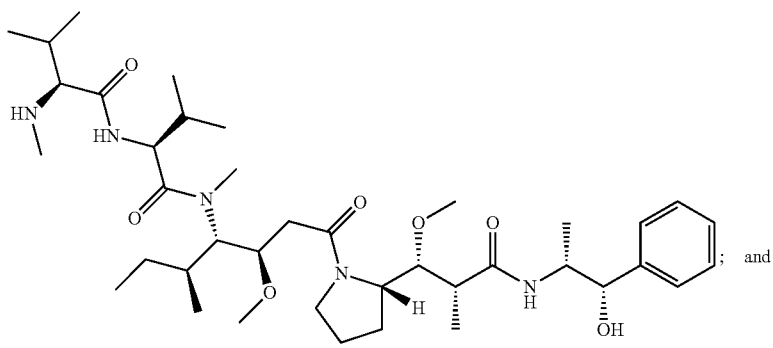
; and
(MMAE)

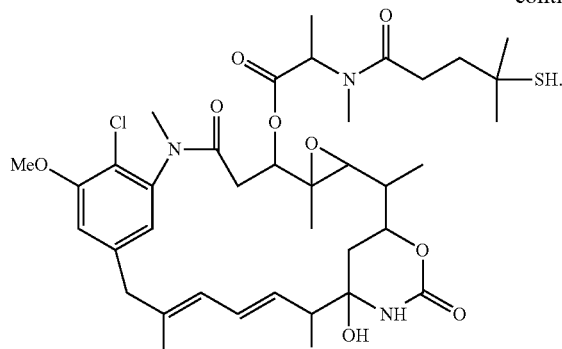

(Maytansinoid DM4)

Administration and Treatment

The nanoparticles and compositions of the invention may be administered to patients by any number of different routes, including enteral or parenteral routes. Parenteral administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes.

Administration be performed e.g. by injection, including depot injection.

The nanoparticles of the invention may be formulated as pharmaceutical compositions that may be in the forms of solid or liquid compositions. Such compositions will generally comprise a carrier of some sort, for example a solid carrier or a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

For intravenous, cutaneous or subcutaneous injection, or injection at the site of affliction, the active ingredient will be in the form of a parenterally acceptable aqueous solution or liquid which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicising agent, preservative or anti-oxidant or other materials well known to those skilled in the art. Such materials should be non-toxic and should not interfere with the efficacy of the active ingredient. The precise nature of the carrier or other material may depend on the route of administration, e.g., intravenous injection.

Preferably, the pharmaceutically compositions are given to an individual in a prophylactically effective amount or a therapeutically effective amount (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Handbook of Pharmaceutical Additives, 2nd Edition (eds. M. Ash and I. Ash), 2001 (Synapse Information Resources, Inc., Endicott, N.Y., USA); Remington's Pharmaceutical Sciences, 20th Edition, 2000, pub. Lippincott, Williams & Wilkins; and Handbook of Pharmaceutical Excipients, 2nd edition, 1994. By way of example, and the compositions are preferably administered to patients in dosages of between about 0.01 and 100 mg of active compound per kg of body weight, and more preferably between about 0.5 and 10 mg/kg of body weight. One benefit of the liver targeting of the nanoparticles of the present invention is that a therapeutically effective dose of the active "payload" may be lower in comparison with the effective dose of the same active when administered as a free drug, e.g., by systematic administration.

The following is presented by way of example and is not to be construed as a limitation to the scope of the claims.

EXAMPLES

Syntheses of Exemplary Ligands and Linkers
Lactose Long Linker Ligand

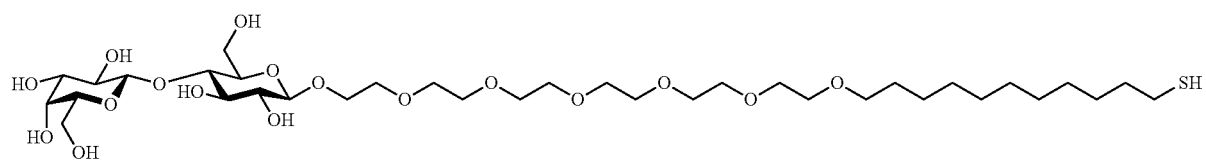

(I)

Also referred to as Lac-O-EG$_6$-C$_{11}$—SH and LacLL, this ligand+linker moiety has the IUPAC name (ω-11-Thioundecyl)-hexaethylene glycolyl β-D-lactoside. It may be synthesised according to A. G. Barrientos, J. M. de la Fuente, T. C. Rojas, A. Fernandez, S. Penades, *Chem. Eur. J.* 2003, 9, 1909-1921.

Glucose Short Linker (Dilution Ligand)

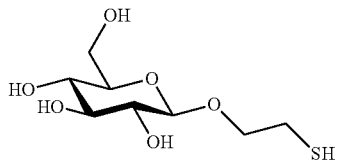

Also referred to Glc-C2-SH, GlcSL, GlcC2, this ligand has the IUPAC name thioethyl β-D-glucopyranoside. It may be synthesised according to Midatech Patent WO 2006/037979 A2 and R. Ojeda, J. L. de Paz, A. G. Barrientos, M. Martin-Lomas, S. Penades, *Carbohydr. Res.* 2007, 342, 448-459.

Amino Linker

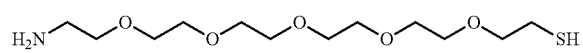

Often referred to the amino linker, this linker is also abbreviated to AL and NH$_2$-EG$_6$-SH. Its IUPAC name is α-amino-ω-thiohexaethylene glycol. It may be synthesised and isolated as the corresponding disulphide from hexaethylene glycol as follows:

The following representative procedures are described.

Hexaetylene glycol (90.0 g, 318.8 mmol) was dissolved in dichloromethane (1 l) and trimethylamine (177 mL, 1275 mmol) and DMAP (1.94 g, 15.9 mmol) were added. The mixture was cooled to 4° C. and tosyl chloride (181.8 g, 956.3 mmol) was added portion wise over 30 minutes. After 10 minutes at around 5° C., the reaction was allowed to warm to room temperature and stirred for 3 hours, then poured into a solution of ethylenediamine in dichloromethane (23.0 ml 344.4 mmol in 630 mL). The organic layer was washed (HCl, 630 ml, 5%; NaHCO$_3$, 5%; brine, each 630 mL), dried over Na$_2$SO$_4$ and concentrated in vacuo to give 217.69 g product which was used without further purification.

This product was dissolved in dimethylformamide (1.4 l) and sodium azide (24.9 g, 382.5 mmol) was added. The reaction was stirred under argon at room temperature for 18 h, then poured into brine (1300 ml) and extracted with ethyl acetate (2×630 ml). The extracts were dried (Na$_2$SO$_4$), concentrated in vacuo and purified (chromatography, SiO$_2$, 15→40% acetone/hexanes) to afford 62.67 g (42%) tosyl azide.

This tosyl azide was dissolved in acetone (630 ml) and potassium thioacetate (20.2 g, 176.5 g) was added. After 19 h, the reaction mixture was poured into brine (1.2 l) and extracted with ethyl acetate (3×600 ml). The extracts were dried (Na$_2$SO$_4$), concentrated and purified (chromatography, SiO$_2$, 0→4% methanol/dichloromethane) to afford 46.1 g thioacetyl azide (93%).

This thioacetyl azide was dissolved in methanol (1.1 l) and sodium methoxide (68.1 g, 1261.5 mmol) was added portion wise. The reaction was stirred (open to the air) for 5 days, then diluted with water (700 ml) and extracted with dichloromethane (2×700 ml). The extracts were dried (Na$_2$SO$_4$), concentrated and purified (chromatography, SiO$_2$, 40% acetone/hexanes) to afford 22.3 g of disulfide (55%).

This disulfide was dissolved in tetrahydrofuran (225 ml) and water (70 ml) and triphenylphosphine (18.6 g, 71.0 mmol) were added. The reaction mixture was stirred at room temperature under argon for 16 h, then diluted with water (50 ml) and washed with ethyl acetate (3×100 ml). The resultant aqueous solution was concentrated in vacuo to afford 11.3 g of amino linker.

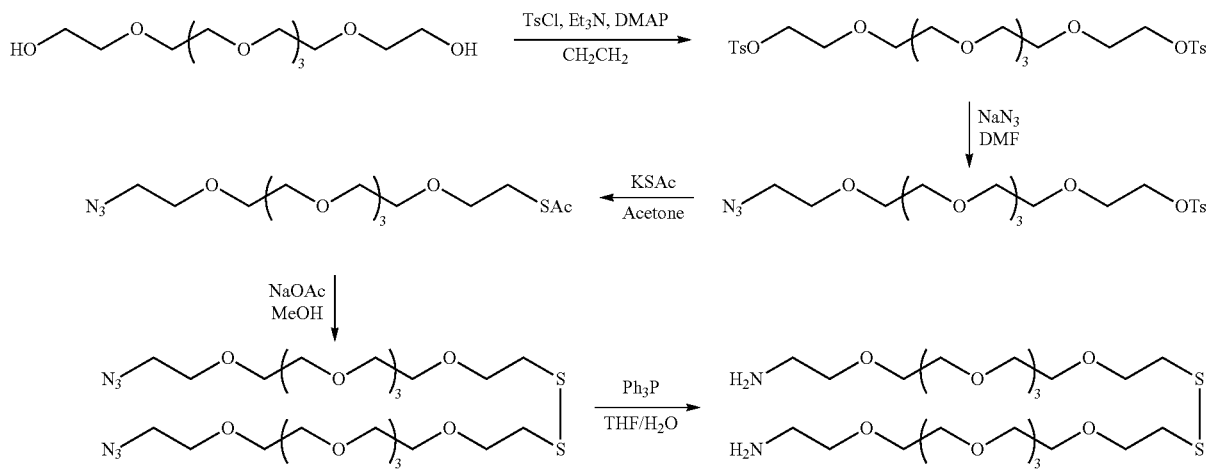

Example 1

Synthesis of Liver Targeting Lactose Long Linker Gold Nanoparticles

The preparation and characterisation of gold nanoparticles loaded with a liver targeting molecule, an attachment linker and a carbohydrate diluent attached to the gold surface is described below.

The ligands LacLL, AL and GlcC2 were used. A hexaethylene glycolyl undecanyl lactose glycoside was chosen as liver targeting moiety while a shorter C2 glucoside was utilised as a diluent moiety. For the attachment of chemotherapeutic pay-loads or other therapeutic or diagnostic molecules like drugs, fluorescent dyes and radio tracer an amino functionalised hexaethylene glycol was used. The coupling to the gold core was realised via a gold sulfur bond.

Gold nanoparticles with different ratios of the liver targeting molecule LacLL were synthesized: LacLL-NP1 (LacLL:AL:GlcC2-9:50:41) and LacLL-NP2 (LacLL:AL:GlcC2-27:50:23).

Figure 3A:
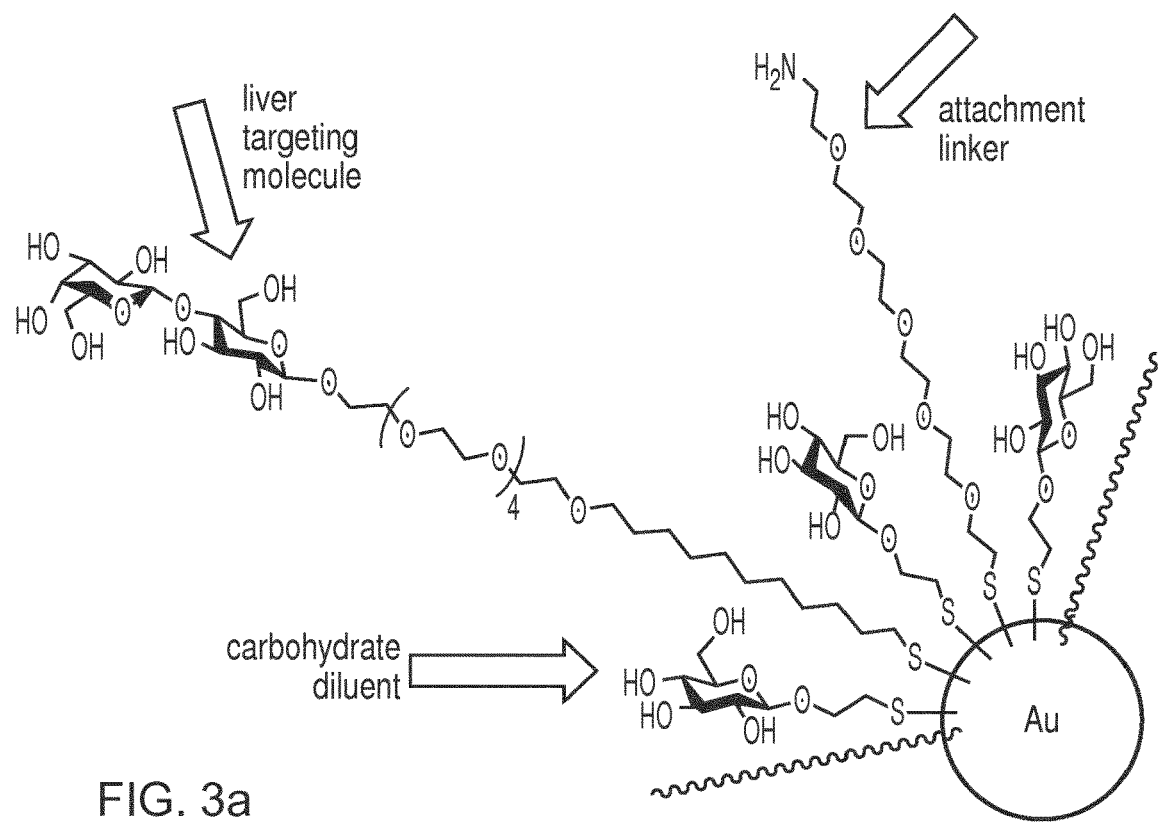
FIG. 3 shows schematic depictions of a LacLL-NP without a payload (a) and the corresponding Pt-LacLL-NP (b) with a Pt-succinate payload.
Figure 4A:
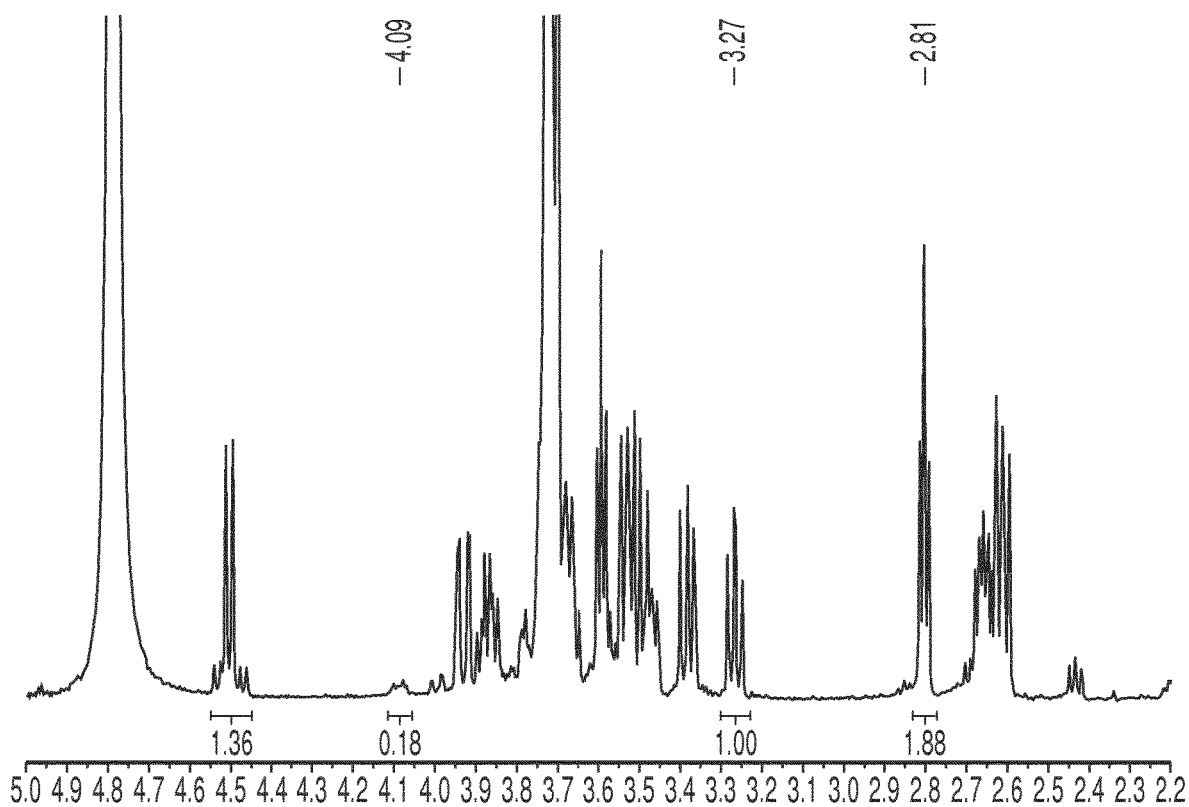
FIG. 4 shows the $^1$H NMR spectra of the nanoparticles of FIG. 3 after KCN etching. (a) shows the spectrum of LacLL-NP1 after KCN etching. Report signals: LacLL=4.09 ppm, AL=2.81 ppm, GlcC2=3.27 ppm; (b) shows the spectrum of Pt-LacLL-NP3 after KCN etching. Report signals: Pt(IV)-suc=2.47 ppm, LacLL=4.08 ppm, AL=2.79 ppm, GlcC2=3.26 ppm.
Figure 5:
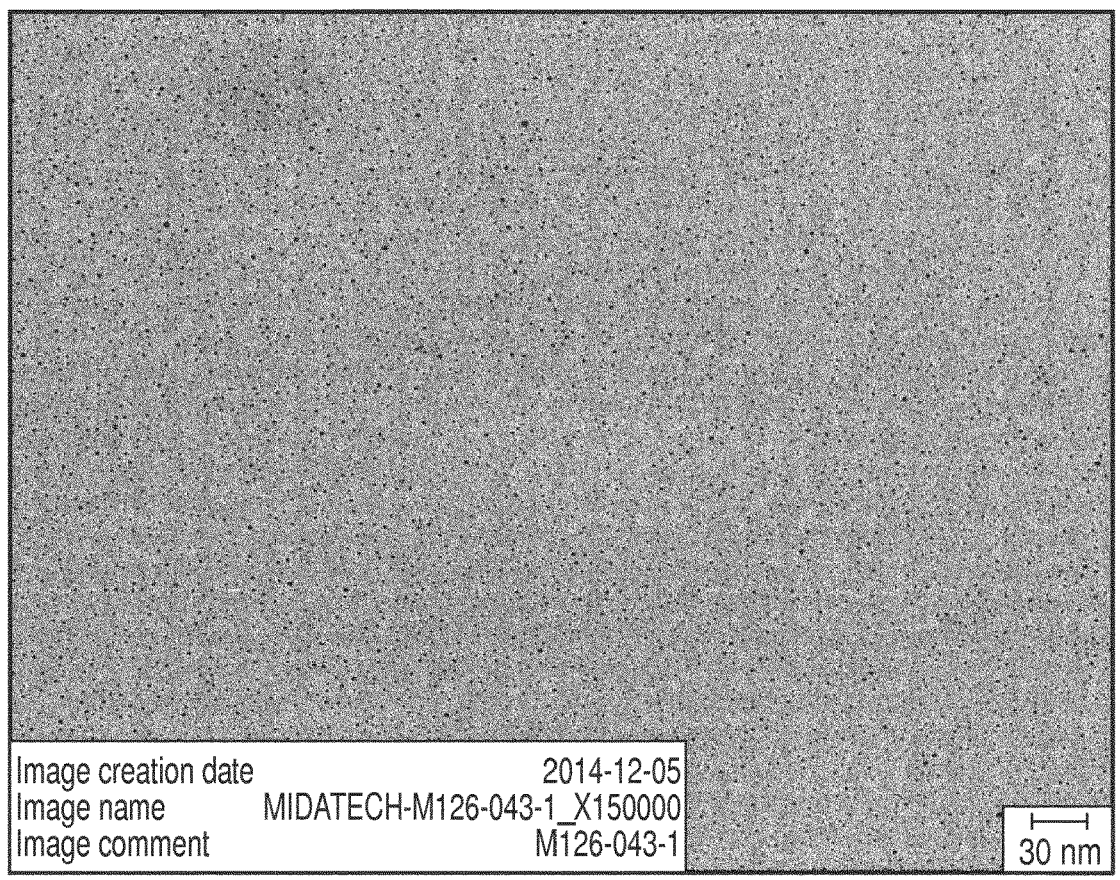
FIG. 5 shows TEM images and data for LacLL-NP1.
Figure 5:
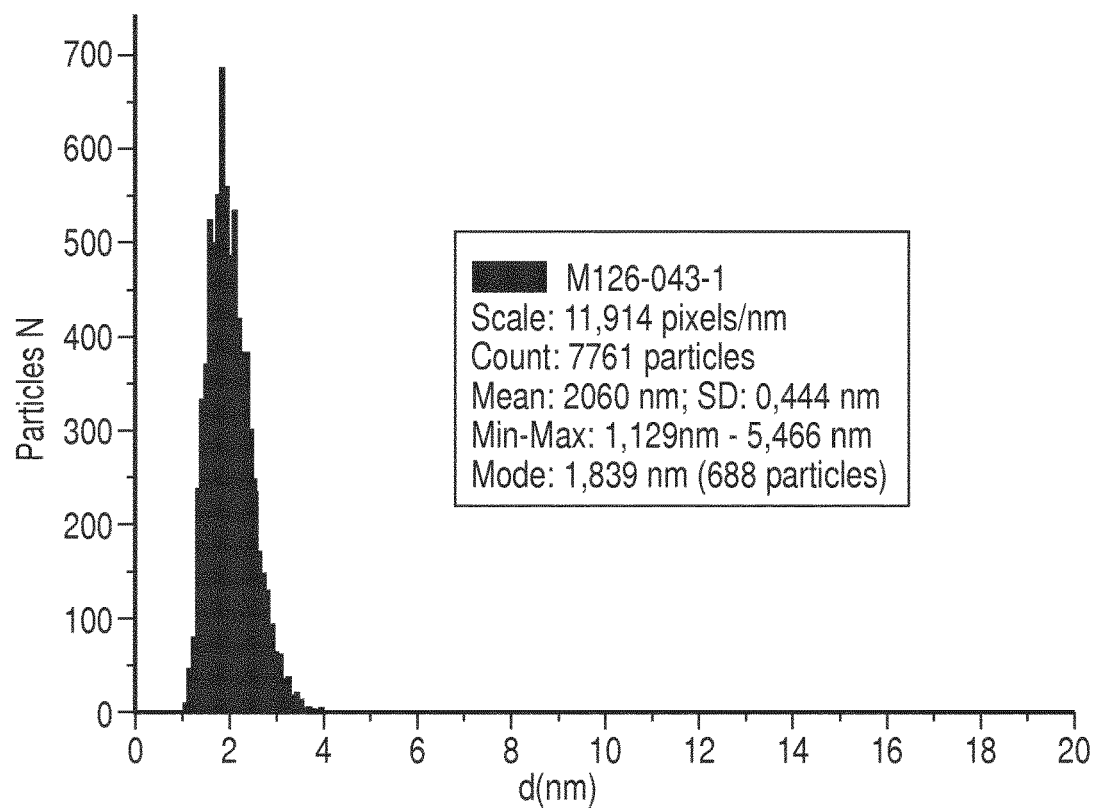

For the preparation of the nanoparticles the ligands LacLL, AL and GlcC2 were dissolved in methanol in the desired proportions and added to a solution of $HAuCl_4$ in water. The gold salt was reduced in the present of thiols/disulfides to gold(0) clusters with a ligand corona. After purification by repeated centrifuge filtration and final dilution to the desired volume nanoparticles were obtained as aqueous solutions (FIG. 3A). The ligand ratio on the nanoparticle was confirmed by $^1H$ NMR. Therefore, an aliquot of the nanoparticle solution was treatment with 0.3 m KCN and 0.1 m KOH in deuterated water after solvent exchange to $D_2O$. After etching of the gold core the spectra of free ligands was acquired and the ligand ratio was determined by report signal integration indicating that the original ratio was maintained on nanoparticles after reaction in the range of error (FIG. 4A). The mean diameters of these constructs, determined using transmission electron microscopy (TEM), were 2.06 nm and 1.98 nm for LacLL-NP1 and LacLL-NP2 (FIG. 5 shows the TEM of LacLL-NP1).

Experimental Section

LAcLL, AL and GlcC2 were synthesized according to references. $HAuCl_4$, $NaBH_4$, KCN, KOH and methanol were purchased from Sigma-Aldrich. All reagents were used without further purification. MilliQ water (18.2 m$\Omega$) was obtained from Simplicity water purification system (Merck Millipore). The nanoparticles were characterized by $^1H$ NMR after KCN/KOH etching, DLS, TEM and zeta potential. The gold concentration of the nanoparticle solution was determined by ICP-MS or MPAES.

For the NMR sample preparation 1 mL solution of the nanoparticles was concentrated and washed (3×2 mL $D_2O$) by centrifuge filtration (Amicon, 10 kDa, 4 mL). The residual NP solution (~200 µL) was incubated with a solution of 0.3 m KCN/0.1 m KOH in $D_2O$ (~400 µL) for 30 minutes at 50° C. The mixture was shortly spun and the supernatant was transferred to a NMR tube. $^1H$ NMR spectra were recorded on a Bruker AVANCE III 500 NMR spectrometer. Chemical shifts were calibrated to the corresponding solvent ($D_2O$=4.79 ppm).

a) LacLL-NP1 (LacLL:AL:GlcC2-9:50:41)

Methanolic solutions of LacLL (0.0410 mmol; 32.5 mg; 1.41 mL), GlcC2 (0.185 mmol; 44.5 mg; 1.58 mL) and AL (0.228 mmol; 67.7 mg; 2.40 mL) were added to 100 mL round bottom flask and diluted with methanol (32.4 mL) to obtain a concentration of 0.012 M of ligands solution. $HAuCl_4$ (60.0 mg; 0.152 mmol; 1 eq.) solution in water (6.09 mL) was then added. The reaction mixture was reduced with $NaBH_4$ (126 mg; 3.34 mmol; 22 eq.) solution in water (3.33 mL) under vortex agitation. The resulting black nanoparticle solution was shaken at room temperature for 35 minutes on an orbital shaker. Over time the nanoparticles precipitated. After finishing the reaction the in solution remaining nanoparticles were spun down by centrifugation (1 min at 4500 rpm) and the precipitate was redissolved in 4 mL of MilliQ water. The aqueous NP suspension was transferred to a previously washed AMICON filter (4 mL, 10 kDa). After concentration the nanoparticles were washed four times with MilliQ water (3-4 mL) by centrifuge filtration. Finally the nanoparticles were collected in a final volume of 6 mL MilliQ water. The nanoparticles were characterized by $^1H$ NMR after KCN/KOH etching, DLS, TEM and zeta potential. The gold concentration of the nanoparticle solution was determined by ICP-MS.

TEM: average diameter 2.06 nm.

b) LacLL-NP2 (LacLL:AL:G1cC2-27:50:23)

Methanolic solutions of LacLL (0.0870 mmol; 69.8 mg; 3.55 mL), GlcC2 (0.0710 mmol; 17.0 mg; 1.67 mL) and AL (0.159 mmol; 47.2 mg; 1.96 mL) were added to 100 mL round bottom flask and diluted with methanol (19.3 mL) to obtain a concentration of 0.012 M of ligands solution. $HAuCl_4$ (40.0 mg; 0.102 mmol; 1 eq) solution in water (4.24 mL) was then added. The reaction mixture was reduced with $NaBH_4$ (84.8 mg; 2.24 mmol; 22 eq) solution in water (2.33 mL) under vortex agitation. The resulting black nanoparticle solution was shaken at room temperature for 35 minutes on an orbital shaker. Over time the nanoparticles precipitated. After finishing the reaction the in solution remaining nanoparticles were spun down by centrifugation (1 min at 4500 rpm) and the precipitate was redissolved in 4 mL of MilliQ water. The aqueous NP suspension was transferred to a previously washed AMICON filter (4 mL, 10 kDa). After concentration the nanoparticles were washed four times with MilliQ water (3-4 mL) by centrifuge filtration. Finally the nanoparticles were collected in a final volume of 4 mL MilliQ water.

The nanoparticles were characterized by $^1H$ NMR after KCN/KOH etching, DLS, TEM and zeta potential. The gold concentration of the nanoparticle solution was determined by ICP-MS.

TEM: average diameter 1.98 nm.

Example 2

Functionalisation of Liver Targeting Lactose Long Linker Gold Nanoparticles with Different Payloads The functionalisation of the attachment linker and characterisation of liver targeting gold nanoparticles equipped with chemotherapeutics and a fluorescent dye is described below.

Figure 3B:
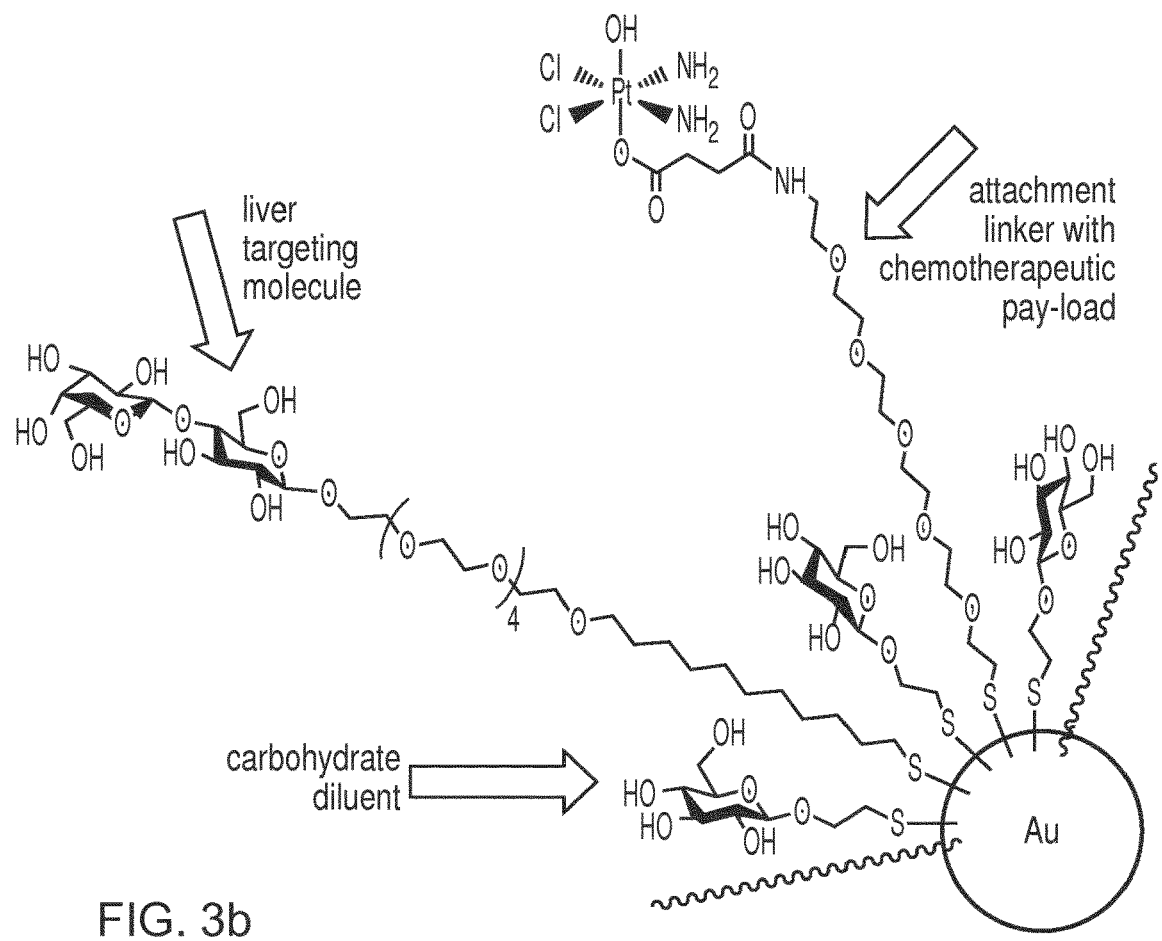
Figure 4B:
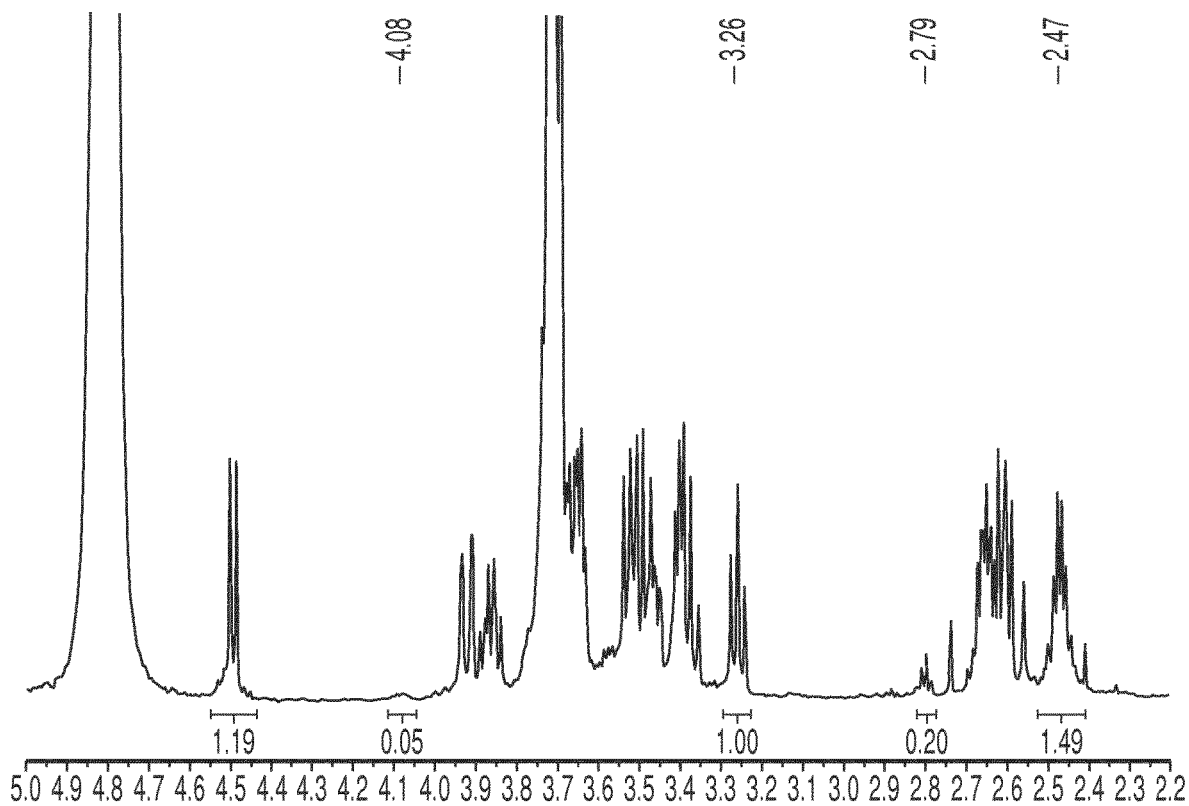

For the functionalisation of the liver targeting nanoparticles two antineoplastic agents were chosen as chemotherapeutics: platinum-(IV)-succinate (Pt(IV)-suc) and doxorubicin. Both chemotherapeutics were coupled to the attachment linker via EDC*HCl/NHS promoted amide bound formation. In the case of Pt(IV)-suc the reaction was performed in DMSO, because the compound was not soluble in aqueous systems. Therefore, the nanoparticle solution was exchanged to DMSO either via lyophilisation or centrifuge concentration and subsequent dilution. Then, the EDC*HCl/NHS pre-activated succinate was reacted with the nanoparticles overnight. Final washings to remove remaining reagents provided an aqueous solution of liver targeting gold nanoparticles with platinum based chemotherapeutic payload (FIG. 3B). The Pt/Au ratio was determined by MPAES to 1/15. The covalent attachment of the drug to the nanoparticle was shown by $^1H$ NMR of the final construct after etching (FIG. 4B). The original signal of the amino methylene group with a chemical shift of 2.81 ppm virtually disappears, while a new multiplet of the succinic ethylene group at 2.47 ppm can observed in the spectrum. The integrals of the reporter signals were not changed indicating corona stability during on nanoparticle manipulations.

For the doxorubicin coupling an inverse attachment strategy was applied. First the amino function was converted to a carboxylic moiety by reaction of the LacLL-NP with succinic anhydride. The carboxylic acid was then reacted with EDC*HCl/NHS in DMSO. After solvent exchange the pre-activated nanoparticle solution was incubated with a doxorubicin solution in HEPES buffer. After purification by centrifuge filtration and final dilution in MES buffer a doxorubicin pay-loaded liver targeting nanoparticle was obtained. The gold and doxorubicin concentration was determined by a colorimetric assay.

The fluorescent dye sulfo-rhodamine B acid chloride was used as a diagnostic mimic. The coupling was realized by a sulphonamide attachment of the sulfonyl chloride moiety of the sulfo-rhodamine B acid chloride with amino function of the attachment linker on the liver targeting gold nanoparticle. The reaction was performed in carbonate buffer at pH 9.3 to obtain labelled particles.

The three experiments showed chemical flexibility for the functionalization of liver targeting gold nanoparticles.

Experimental Section

Sulfo-rhodamine B acid chloride, EDC*HCl, NHS and DMSO were purchased from Sigma-Aldrich. Pt(IV)-succinate was purchased from Charnwood Molecular. Doxorubicin was purchased from LC Labs. All reagents were used without further purification. MilliQ water (18.2 m$\Omega$) was obtained from Simplicity water purification system (Merck Millipore). The nanoparticles were characterized by $^1$H NMR after KCN/KOH etching, DLS, TEM and zeta potential. The gold concentration of the nanoparticle solution was determined by ICP-MS or MPAES.

For the NMR sample preparation 1 mL solution of the nanoparticles was concentrated and washed (3×2 mL $D_2O$) by centrifuge filtration (Amicon, 10 kDa, 4 mL). The residual NP solution (~200 µL) was incubated with a solution of 0.3 m KCN/0.1 m KOH in $D_2O$ (~400 µL) for 30 minutes at 50° C. The mixture was shortly spun and the supernatant was transferred to a NMR tube. $^1$H NMR spectra were recorded on a Bruker AVANCE III 500 NMR spectrometer. Chemical shifts were calibrated to the corresponding solvent ($D_2O$=4.79 ppm).

a) Pt-LacLL-NP3

5 mL of aqueous LacLL-NP1 nanoparticle solution (low concentration of targeting ligand) (21.4 µmol reactive AL) was concentrated by centrifugation (2×15 minutes at 4500 rpm) in an Amicon filter (4 mL, 10 kDa) and diluted to a volume of 2.5 mL with DMSO. Prior to addition to a solution of Pt(IV)-succinate (22.9 mg, 52.9 µmol) in DMSO (528 µL, 0.1 m) a solution of EDC*HCL (12.2 mg, 63.4 µmol) in DMSO (127 µL, 0.5 m) and NHS (7.29 mg, 63.4 µmol) in DMSO (63.4 µL, 1.0 m) were mixed and incubated for 15 minutes at room temperature. After 30 minutes of pre-activation the reaction mixture was added to the nanoparticle solution and the mixture was shaken on an orbital shaker at room temperature overnight. The reaction solution was diluted with 25 mL MilliQ water and concentrated and repeatedly washed with MilliQ water. The black residue was collected in 5.00 mL MilliQ water. The nanoparticles were characterized by $^1$H NMR after KCN/KOH etching, DLS, TEM and zeta potential. The gold and platinum concentration of the nanoparticle solution was determined by ICP-MS. [Au], MPAES: 2.84 mg/mL; [Pt], MPAES: 0.19 mg/mL.

b) Doxo-LacLL-NP4

Succination of amino function on LacLL-NP: 8.0 mL of aqueous LacLL-NP1 nanoparticle solution (low concentration of targeting ligand) (33.8 µmol reactive AL) was concentrated by centrifugation (15 minutes at 4500 rpm) in an Amicon filter (15 mL, 10 kDa) and diluted to a volume of 8.0 mL with DMSO. Succinic anhydride (16.9 mg, 169 µmol) was dissolved in DMSO (564 µL) to obtain a 0.5 m solution and added to the nanoparticle solution. The reaction mixture was shaken on an orbital shaker at room temperature overnight. The reaction solution was diluted with 25 mL MilliQ water and concentrated and repeatedly washed with MilliQ water. The black residue was collected in 5.00 mL MilliQ water. The nanoparticles were characterized by $^1$H NMR after KCN/KOH etching, DLS, TEM and zeta potential. The gold and platinum concentration of the nanoparticle solution was determined by ICP-MS.

Doxorubicin attachment to succinated attachment linker of LacLL-NP: 3.0 mL of aqueous LacLL-NP nanoparticle solution (10.0 µmol reactive succinated AL) was concentrated by centrifugation (15 minutes at 4500 rpm) in an Amicon filter (4 mL, 10 kDa) and diluted to a volume of 3.0 mL with DMSO. A solution of EDC*HCl (4.82 mg, 25.1 µmol) and (5.75 mg, 50.0 µmol) in DMSO (416 µL) which was incubated for 15 minutes was added to the nanoparticle solution and the mixture was shaken for 2 hours at room temperature on an orbital shaker. The nanoparticle solution was diluted with water (80 mL) was filtered by centrifugation, diluted with HEPES buffer (pH 7.8, 25.0 mL) and a solution of doxorubicin (2.50 mL, 2.00 mg/mL in HEPES 20 mM) was added immediately. The coupling reaction was incubated at room temperature for 1 hour. The nanoparticles coupled with DOX were purified with MilliQ water by centrifuge filtration (Amicon, 15 mL, 10 kDa). The residual solution was collected in MES buffer (3.0 mL). The nanoparticles were characterized by $^1$H NMR after KCN/KOH etching, DLS, TEM and zeta potential. The gold concentration of the nanoparticle solution was determined by ICP-MS. [Au], colorimetric: 1.05 mg/mL; [Doxo], colorimetric: 0.66 mg/mL.

c) sRhoB-LacLL-NP5

3 mL of aqueous LacLL-NP1 nanoparticle solution (0.609 µmol nanoparticle) (low concentration of targeting ligand) was concentrated by centrifuge filtration (AMICON, 4 mL, 10 kDa) and washed once with $Na_2CO_3$/$NaHCO_3$ buffer (0.1 M, pH 9.3). The residual solution was solved in 1.5 mL of the buffer. To the NP solution a sulfo-rhodamine B acid chloride solution in DMF (133 µL, 9.14 µmol, 5.27 mg) was added and mixture was shaken on an orbital shaker at room temperature overnight shielded from daylight. The reaction mixture was transferred to a previously washed AMICON filter (4 mL, 10 kDa). Nanoparticle solution was centrifuged and repeatedly washed three times with $Na_2CO_3$/$NaHCO_3$ buffer (0.1 M, pH 9.3) and repeatedly with Milli-Q water until the filtrate appears colorless. Finally, the nanoparticles were collected in 3 mL Milli-Q water. The nanoparticles were characterized by $^1$H NMR after KCN/KOH etching, DLS, TEM and zeta potential. The gold concentration of the nanoparticle solution was determined by ICP-MS.

Example 3

Liver Targeting of Nanoparticles Demonstrated In Vivo

The liver targeting properties of lactose long linker gold nanoparticles could be shown by comparison of different nanoparticle constructs in an in vivo biodistribution study. Two lactose long linker nanoparticles with a high and a low content of the liver targeting molecule (LacLL-NP1 (low)+ LAcLL-NP2 (high)), two similar lactose short linker nanoparticles (LacSL-NP1 (low)+LacSL-NP2 (high)) (the lactose is linked to a C2 linker), and non-targeting nanoparticle (Glc-NP), respectively, were intravenously injected to mice.

Figure 6:
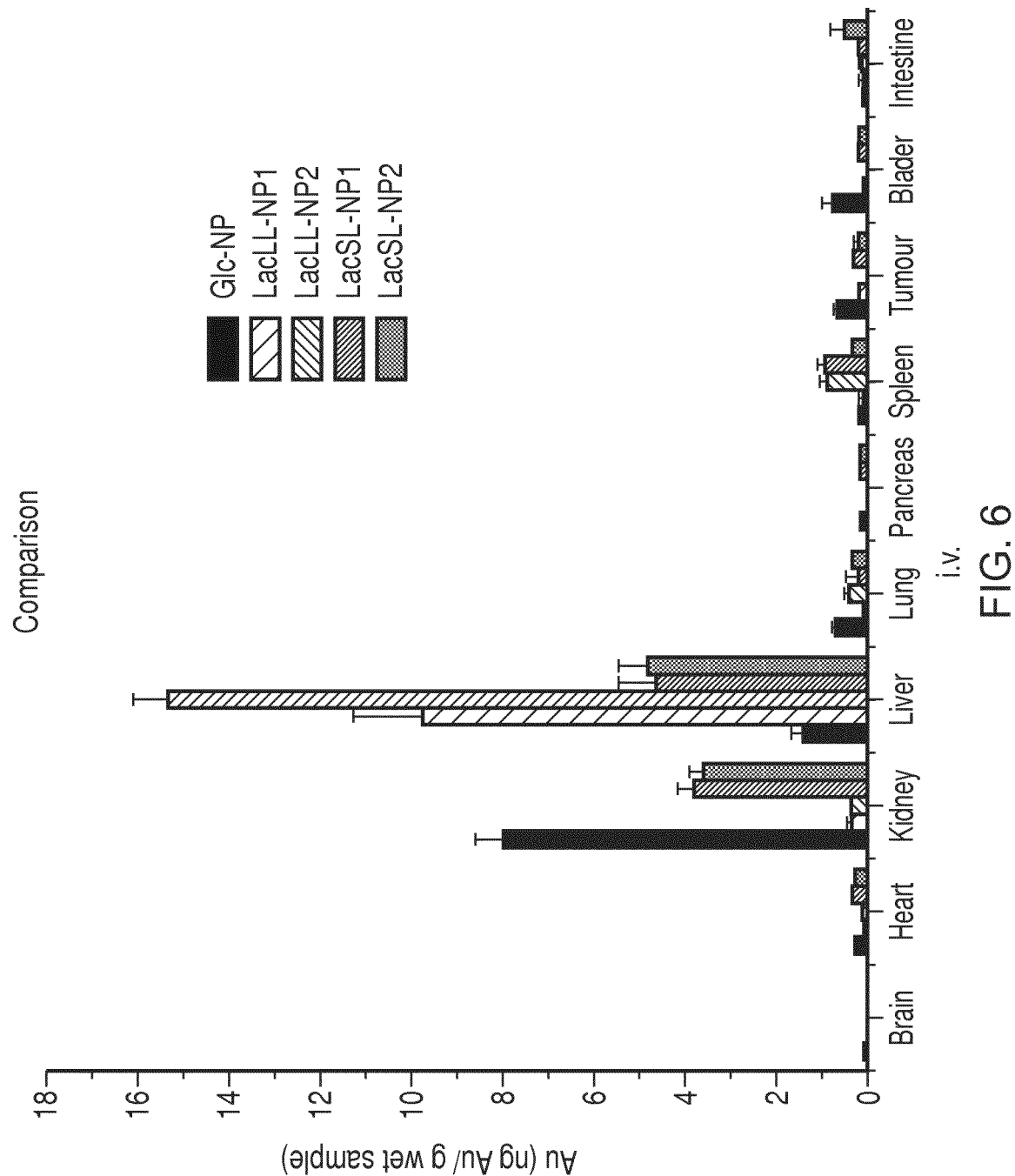
FIG. 6 shows ICP-MS results for accumulation of rhodamine-conjugated GNPs in various organs in the body. From left to right, the x axis reads: brain, heart, kidney, liver, lung, pancreas, spleen, tumour, bladder, and intestines. MBLB-0126-012 is the control, MBLB-126-078 is LacLL-NP2, MBLB-135-042 is LacLL-NP1, MBLB-126-082 is LacSL-NP1, and MBLB-126-084 is LacSL-NP2.

After 90 minutes circulation time the animals were sacrificed, the main organs were harvested and analysed by ICP-MS to determine the gold concentration in the organs. The plotting of these data provided a biodistribution map for the different constructs (FIG. 6). As expected, the liver targeting constructs were mainly found in the liver, whereas the non-targeting nanoparticle was accumulated in the kidneys. It was observed that the linker length of the liver targeting molecule influences the liver uptake of the gold nanoparticle. For the short linker version 42-46% of the total found gold amount was present in the liver. By contrast, for the long linker constructs almost all gold was detected in the liver (up to 91%).

This experiment demonstrates that suitable payloads can highly efficient directed to the liver using liver targeting lactose long linker gold nanoparticles.

Experimental Section

Cell Lines and Transfection

Hepatocarcinoma cell line, HepG2, cells were grown in DMEM (Sigma Aldrich) supplemented with 10% FCS (Gibco) at 37° C., 95% air and 5% $CO_2$, in 10-cm petri dishes (BD), washed with PBS 1× (Sigma Aldrich) and passaged upon treatment with Trypsin.EDTA 0.05% (Gibco). Viable cells were counted in a hemocytometer in a trypan blue exclusion assay. HepG2 cells were regularly tested for mycoplasma using a set of primers common to all members of genus Mycoplasma (Choppa et al, 1998). Cells were seeded at a density of 2-3 $10^4$ cells/$cm^2$ in a 6-well plate and subsequently transfected with 1:3 and 1:5 molar ratios of pEGFP-Luc vector (Clontech) and PEI25 (Sigma-Aldrich). Upon transfection, cells were selected by adding 800 μg/μL G418 to the culture medium for forty-eight hours. Subsequently, cells were maintained in fresh medium and grown until confluence. In order to assess the in vitro bioluminescence signal a simple luciferase assay with the aid of a Mithras multimode plate reader by adding D-Luciferase to cell lysates in CCLR buffer was performed (25 mM Tris.HCl pH 7.8, 2 mM DTT, 2 mM EGTA, 10% glycerol, 1% Triton X-100).

Animal Housing

Seventy female BALB/c nude mice (6 weeks old) were purchased from an authorized provider (Janvier Labs). All mice were housed in laminar-flow cabinets under specific pathogen-free conditions at room temperature with a 12-hour light/dark cycle and fed with pellets and water ad libitum. The Experimental Animal Committee of USC approved the animal study; consequently, all animal experiments meet the Animal Welfare guidelines.

Xenografts & In Vivo Near-Infrared Fluorescence Imaging

Log growth-phase of HepG2 cells ($10^5$ cells in 0.1 ml PBS) were injected to subcutaneously into the left flank of athymic nude mice (n=6 each experimental group) to establish the model of tumor-bearing mice. Tumour implantation was regularly checked by visual inspection and finally confirmed by registration of bioluminescent signal in an IVIS Spectrum (Caliper LifeSciences). D-Luciferin was administered (150 mg/kg) in order to co-localize the bioluminescence in tumour cells with the fluorescent NPs. Mice bearing tumours were be split into 5 groups (control group included), six mice each. Tumour volume were calculated by the formula: [(length$^2$×width)/2] (Soengas et al., 1999). Once the tumours reached a volume of 400 $mm^3$ nanoparticles were administered i.v.

In vivo fluorescence imaging was acquired using an IVIS Spectrum (Caliper LifeSciences) for detection of the rhodamine-conjugated GNPs at 0 min, 45 min, and 90 min after injection. Mice were anesthetized using isoflurane during image acquisition, and upon the acquisition of fluorescence/bioluminescence images were euthanized (at 90 min after injection) and their organs (brain, lungs, heart, liver, spleen, pancreas, gut, bladder and kidneys) and the tumor harvested for subsequent ICP-MS analysis.

| | ICP-MS results | | | | | | | | |
|---|---|---|---|---|---|---|---|---|---|
| | μg Au/g wet sample | | | | | | | | |
| | Brain | Heart | Kidney | Liver | Lung | Pancreas | Spleen | Tumour | Bladder | Intestine |
| Glc-NP | 0.020 | 0.236 | 7.988 | 1.419 | 0.710 | 0.138 | 0.188 | 0.691 | 0.800 | 0.112 |
| LacLL-NP1 | 0.006 | 0.066 | 0.286 | 15.322 | 0.451 | 0.030 | 0.909 | 0.039 | 0.019 | 0.135 |
| LacLL-NP2 | 0.002 | 0.064 | 0.360 | 9.749 | 0.072 | 0.023 | 0.092 | 0.188 | 0.085 | 0.114 |
| LacSL-NP1 | 0.015 | 0.292 | 3.807 | 4.622 | 0.213 | 0.172 | 0.938 | 0.303 | 0.218 | 0.208 |
| LacSL-NP2 | 0.013 | 0.277 | 3.571 | 4.826 | 0.329 | 0.167 | 0.326 | 0.230 | 0.205 | 0.537 |

Example 4

Figure 7:
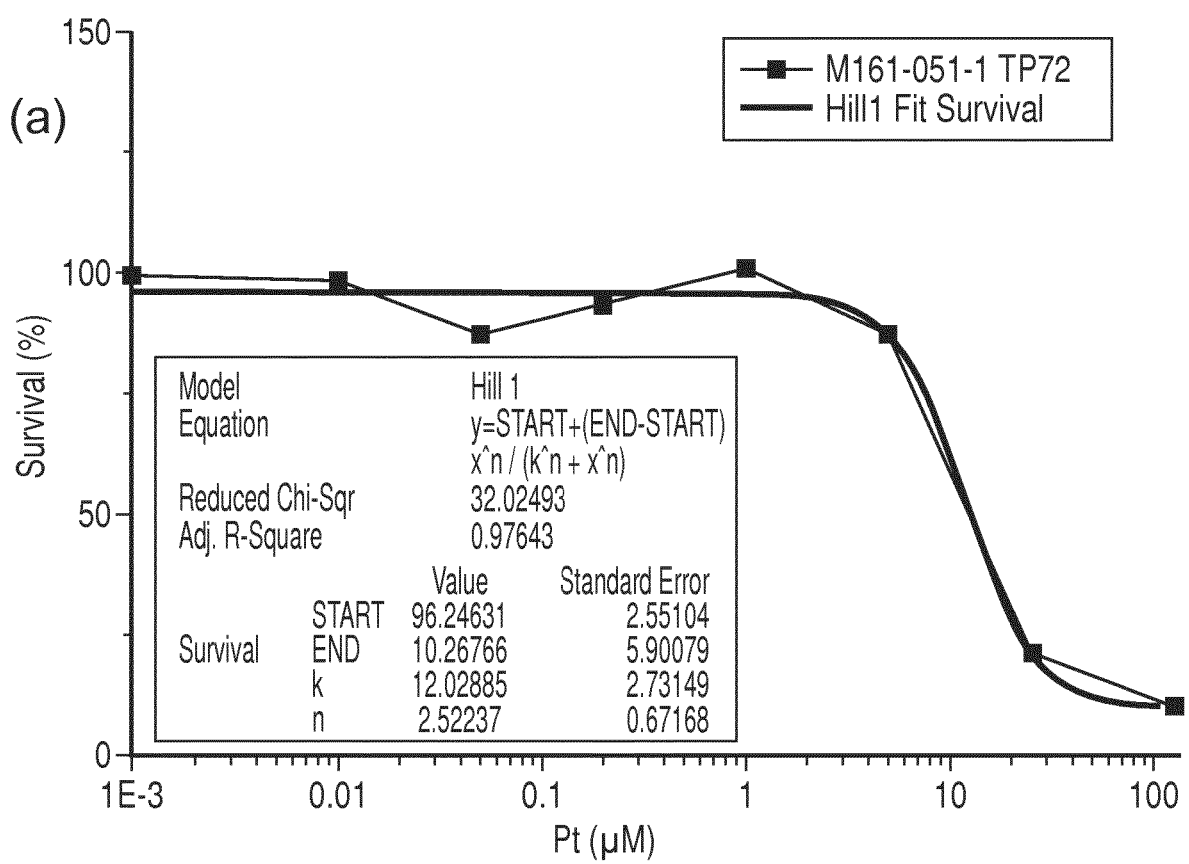
FIG. 7 shows MTT cell viability assay results 72 h after treatment with (a) Pt-LacLL-NP, (b) free Pt, (c) Doxo-LacLL-NP and (d) free doxorubicin.
Figure 7:
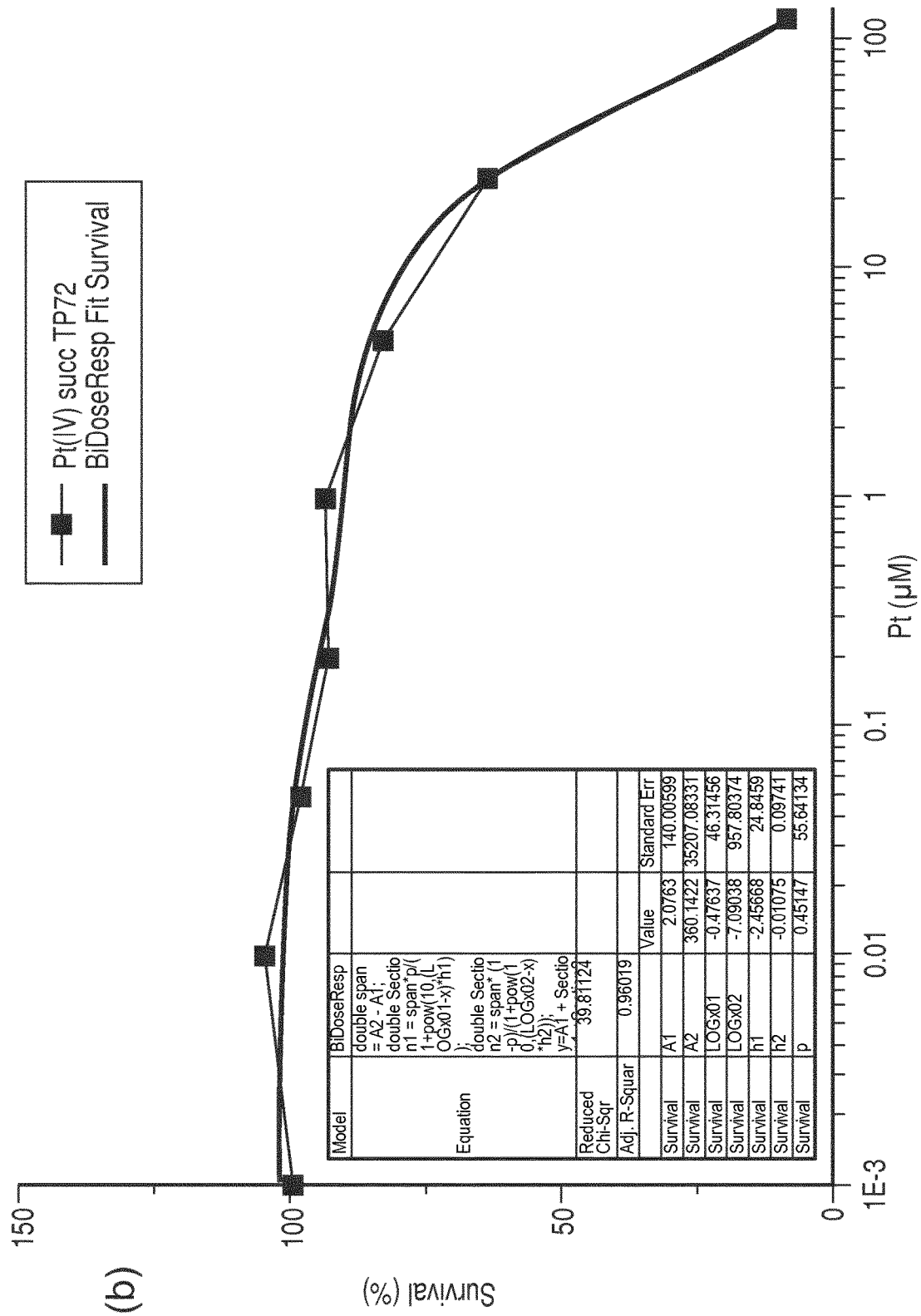
Figure 7:
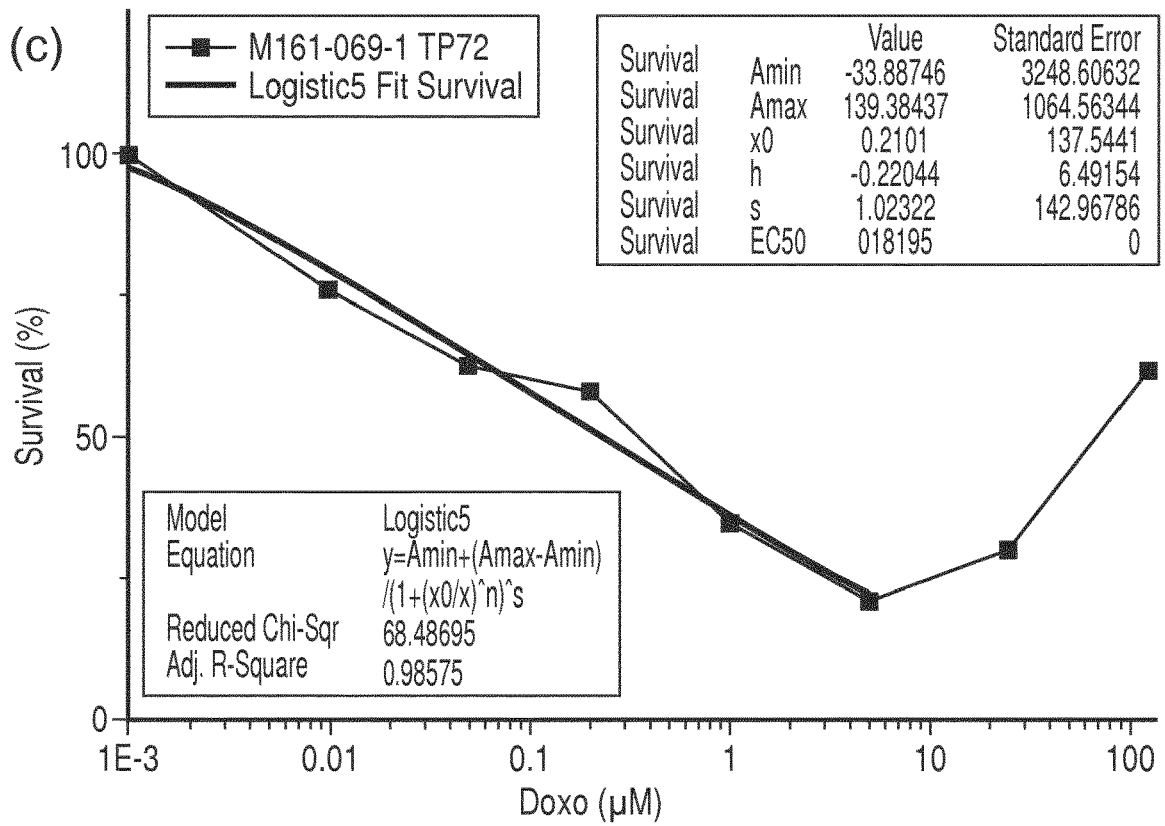
Figure 7:
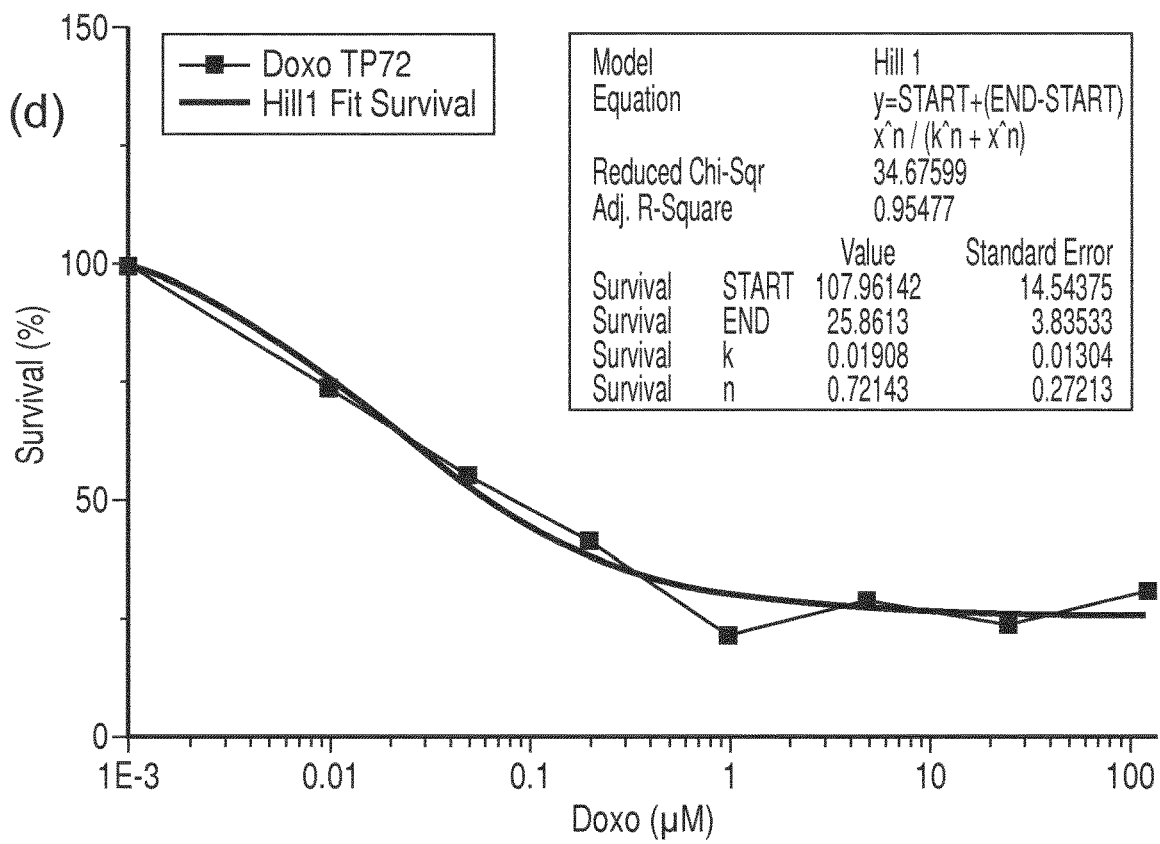

In Vitro Cytotoxicity with Liver Targeting Lactose Long Linker Gold Nanoparticles Carrying a Chemotherapeutic Pay Load The cytotoxicity of liver targeting lactose long linker gold nanoparticles pay-loaded with the chemotherapeutics Pt(IV)-succinate (Pt-LacLL-NP+platinum) and doxorubicin (Doxo-LacLL-NP+doxorubicin) was tested in comparison with the free drug in a MTT (3-(4,5-dimethylthiazol-2-yl)-2,5-diphenyltetrazolium bromide) cell viability assay (FIG. 7). The human hepatocellular carcinoma cell line HepG2 was used in the assay.

In the case of the platinum based antineoplastic agent Pt(IV)-succinate, it was demonstrated that the Pt-LacLL-NP is more potent than the free drug. For the nanoparticle, an IC50 value of 12.8 μM was observed, whereas for the free drug a value of 38.6 μM could be found. For doxorucibin, the free compound showed a slightly higher cytotoxicity in comparison to the pay-loaded nanoparticle. The attachment of the drug to the nanoparticle maintained the chemotherapeutic activity and allows the use of liver targeting lactose long linker gold nanoparticles as a drug delivery system.

| MTT assay results | |
|---|---|
| Compound | IC50 (μM) |
| Pt-LacLL-NP | 12.78 |
| Platinum | 38.61 |

-continued

MTT assay results

| Compound | IC50 (µM) |
|---|---|
| Doxo-LacLL-NP | 0.24 |
| Doxorubicin | 0.06 |

Experimental Section

Cell Seeding In 96-Well Microtiter Plates

HepG2 cells were grown in a T-75 flask. For the transfer of the cell the medium was removed from the flask and the cells were trypsinated for 5 minutes. The cells were collected in a Falcon tube and diluted with complete cell medium. The cell counting was conducted in a Neubauer chamber. A cell solution was prepared to seed 4000 cells per well (200 µL per well). The microtiter plate was incubated for 24 h at 37° C.

Treatment of Seeded HepG2 Cell

For each NP and drug, formulations in cell medium were prepared. The compounds were tested in different concentrations (0.01, 0.05, 0.2, 1, 5, 25 and 125 µM based on drug amount). For the treatment, the cell medium was removed from all wells and exchanged for drug formulations. 200 µl of treatments per triplicate was added to each well. The microtiter plates were incubated for 24 h, 48 h and 72 h at 37° C.

MTT Measurement 24 h, 48 h and 72 h After Treatment 1.5 mL MTT solution (8.0 mg in 1.6 mL DMSO) was diluted with complete cell medium (phenol-red free). The treatment cell medium was removed from the microtiter plate, the wells were washed with 100 µL PBS and 100 µL of the MTT reactive solution was added to each well. After one hour incubation at 37° C. the MTT solution was removed and 100 µL DMSO was added to dissolve the formazan dye. Absorbance was measured at 570 nm.

Statistical Analysis and IC50 Calculation

Data were analysed using OriginPro8. The normalized data were plotted and the curve was fitted using a non-linear regression curve fit (sigmoidal dose-response curve with variable slope). The Absolute IC50 values were obtained by interpolation.

Example 5

Selection of Targeted GNPs and HCC Targeting In Vitro

Several base/peptide targeted GNPs were screened in vitro. GNPs having a mixed corona comprising galactose-C2-SH (Gal-C2) ligands and HSPEG8COOH were synthesised according to methodology analogous to that described above in Examples 1 and 2, with however galactose-C2-SH replacing glucose-C2-SH and HSPEG8COOH (also abbreviated SH-EG$_8$-COOH or SH—(OCH$_2$CH$_2$)$_8$—COOH) replacing the amino linker NH$_2$-EG$_6$-SH.

The Au@Gal-C2:HSPEG8COOH GNPs were found to exhibit lower non-specific binding (normal:tumour cells) and good plasma circulation in vivo. The corona of Gal-C2 and HSPEG8COOH was therefore selected for HCC targeting studies using glypican-3 binding peptides.

Figure 8:
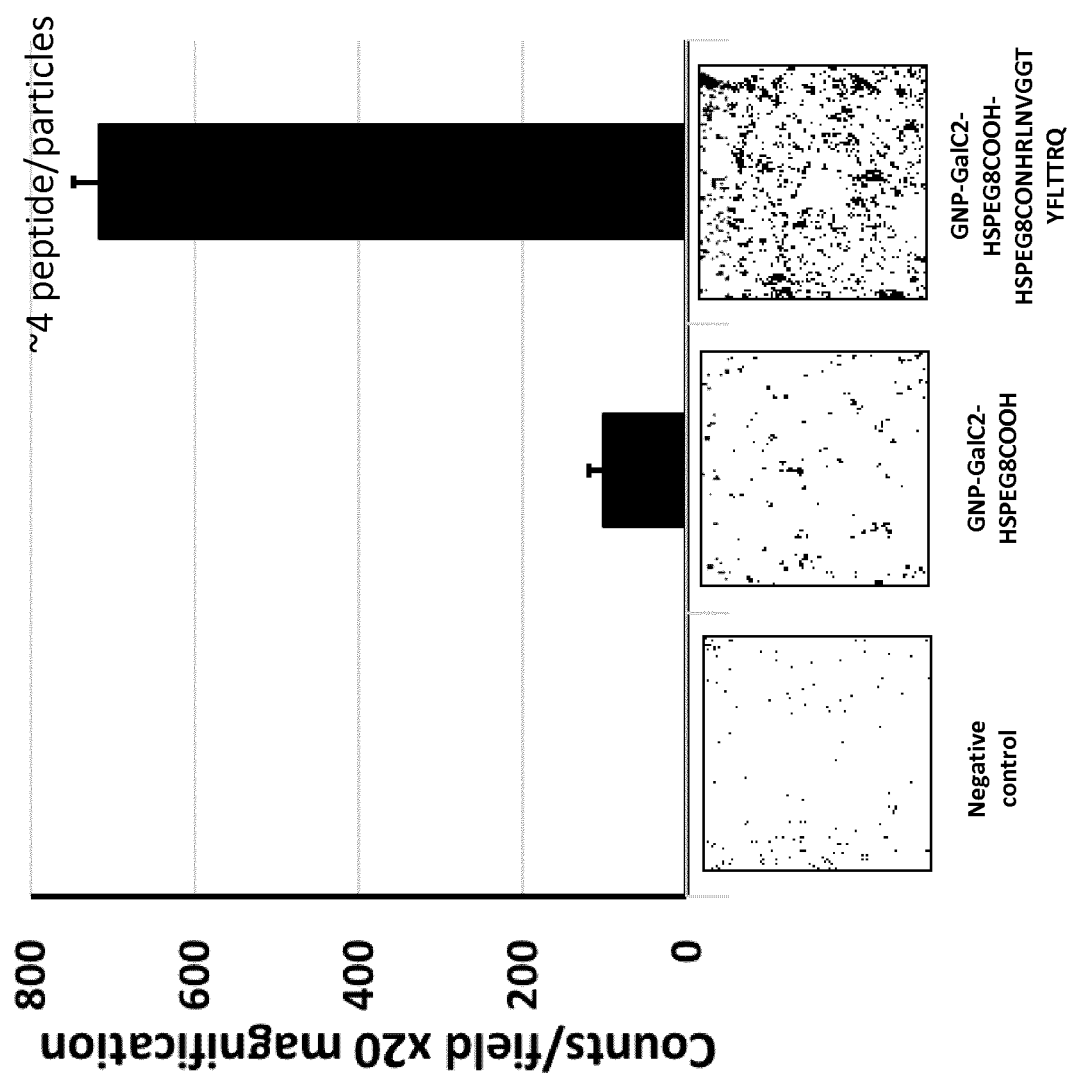
FIG. 8 shows in vitro targeting of GNPs to HCC cells measured as counts per field at 20× magnification. The left-hand panel shows a lack of counts exhibited by the negative control. The middle panel and bar shows counts for GNPs having a corona of galactose-C2 ligands and HSPEG8COOH ligands. The right-hand panel and bar shows counts for GNPs with a corona of galactose-C2 ligands and HSPEG8COOH ligands, in which a proportion of the HSPEG8COOH ligands have conjugated thereto the glypican-3-binding peptide, RLNVGGTYFLTTRQ (SEQ ID NO: 1), via its N-terminus (approx. 4 peptide molecules per nanoparticle). It is immediately evident that the GNPs having the glypican-3-binding peptide exhibit significantly increased targeting to HCC cells compared with GNPs lacking the glypican-3-binding peptide (approx. 7-fold increased targeting).

The glypican-3 peptide described in U.S. Pat. No. 8,388,937B2 (the contents of which are expressly incorporated herein by reference)—see SEQ ID NO: 1 thereof, which has the amino acid sequence: RLNVGGTYFLTTRQ (SEQ ID NO: 1) was linked to the terminal COOH group of a proportion of the HSPEG8COOH ligands via the N-terminus of said peptide. In a "high loading" GNP construct (see row 1 in the table below), approximately 4 peptides were linked per nanoparticle core. The "high loading" Au@Gal-C2:HSPEG8COOH:HSPEG8CONHRLNVGGTYFLTTRQ GNPs were found to exhibit approximately 7-fold targeting relative to the base GNP lacking the RLNVGGTYFLTTRQ peptide (see FIG. 8 and the first row of the following table). The "low loading" Au@Gal-C2:HSPEG8COOH:HSPEG8CONHRLNVGGTYFLTTRQ GNPs (see row 3 of the following table) exhibited approximately 4.6-fold targeting relative to the base GNP lacking the RLNVGGTYFLTTRQ peptide.

| GNP-Construct | Fold-targeting (over base particle) |
|---|---|
| GNP-GalC2-HSPEG8COOH-HSPEG8CONHRLNVGGTYFLTTRQ "high loading" | 7.1 |
| GNP-GalC2(50)-AL(50)-(Ac)YFLTTRQ | 5.0 |
| GNP-GalC2-HSPEG8COOH-HSPEG8CONHRLNVGGTYFLTTRQ "low loading" | 4.6 |

Further investigation has been carried out in which the orientation and/or terminal capping of the linked RLNVGGTYFLTTRQ peptide was evaluated. In particular, RLNVGGTYFLTTRQ (attached to PEG8COOH via the N-terminus, free COOH terminus—described above) and RLNVGGTYFLTTRQ-NH2 (attached to PEG8COOH via the N-terminus, primary amide terminus replacing the standard C-terminus).

A further construct that has been investigated comprises a mixed corona of galactose-C2-SH and amino linker (also known as "AL" or NH$_2$-EG$_6$-SH) in approximately 50:50 ratio. The RLNVGGTYFLTTRQ peptide was attached to the amino linker via the C-terminus of the peptide or by using an acyl-N-terminal version of the peptide and attaching the acyl-N-terminus of the peptide to the amino linker. Two methods were employed: (1) the peptide was attached to GNP-AL via the C-terminus (giving a positive particle); or (2) the peptide was attached to AL-SH in a first step and the SH-EG$_6$-NHCO-RLNVGGTYFLTTRQ used as a ligand in the nanoparticle synthesis giving a negative particle. The resulting particle may be represented as: Au@GalC2:AL:AL-(Ac)-RLNVGGTYFLTTRQ.

A Further glypican-3-binding peptide described in U.S. Pat. No. 8,388,937B2 (the contents of which are expressly incorporated herein by reference)—see SEQ ID NO: 10 thereof, which has the amino acid sequence: YFLTTRQ (SEQ ID NO: 2) was linked to GNP ligands as follows. A GNP having a mixed corona of galactose-C2-SH and amino linker (NH$_2$-EG$_6$-SH) in approximately 50:50 ratio had the YFLTTRQ peptide linked to the amino linker via an acyl N-terminus of the YFLTTRQ peptide to yield a GNP which may be represented by the following formula: Au@GalC2:AL:AL-(Ac)-YFLTTRQ. Further GNPs produced or contemplated herein include: Au@GalC2:HSPEG8CONH-YFLTTRQ (attached to PEG8COOH via the N-terminus, free COOH terminus) and Au@GalC2:HSPEG8CONH-YFLTTRQ-NH2 (attached to PEG8COOH via the N-terminus, primary amide terminus). As can be seen from row 2 of the above table, the GNP Au@GalC2:AL:AL-(Ac)-YFLTTRQ exhibited approximately 5-fold targeting to HCC cells compared with the base nanoparticle, lacking the YFLTTRQ peptide. These results therefore show that glypican-3 binding peptides contribute to HCC targeting and that higher peptide loading (i.e. more glypican-3 binding peptides per nanoparticle) increases HCC targeting further.

Example 6

GLY-3 Targeted GalC2 GNP Shows HEPG2 Cell Toxicity with a DM4 Payload

The following GNP constructs were synthesised in order to assess their tumour cell killing capability against HepG2 (liver hepatocellular carcinoma) cells:

GNPs with a corona of galactose-C2 and HSPEG8COOH ligands (40:60 ratio), which may be represented by Au@GalC2:HSPEG8COOH.

GNPs with a corona of galactose-C2, HSPEG8COOH and maytansinoid DM4 ligands, which may be represented by Au@GalC2:HSPEG8COOH:DM4.

GNPs with a corona of galactose-C2, HSPEG8COOH and maytansinoid DM4 ligands, wherein a proportion of the HSPEG8COOH ligands are conjugated to the N-terminus of the glypican-3-binding peptide RLNVGGTYFLTTRQ (SEQ ID NO: 1) <1 peptide per nanoparticle. The GNPs may be represented by: Au@GalC2:DM4:HSPEG8COOH:HSPEG8CONHRLNVGGTYFLTTRQ.

Free maytansinoid DM4 was also used as a positive control in the HepG2 cell toxicity experiments.

Figure 9:
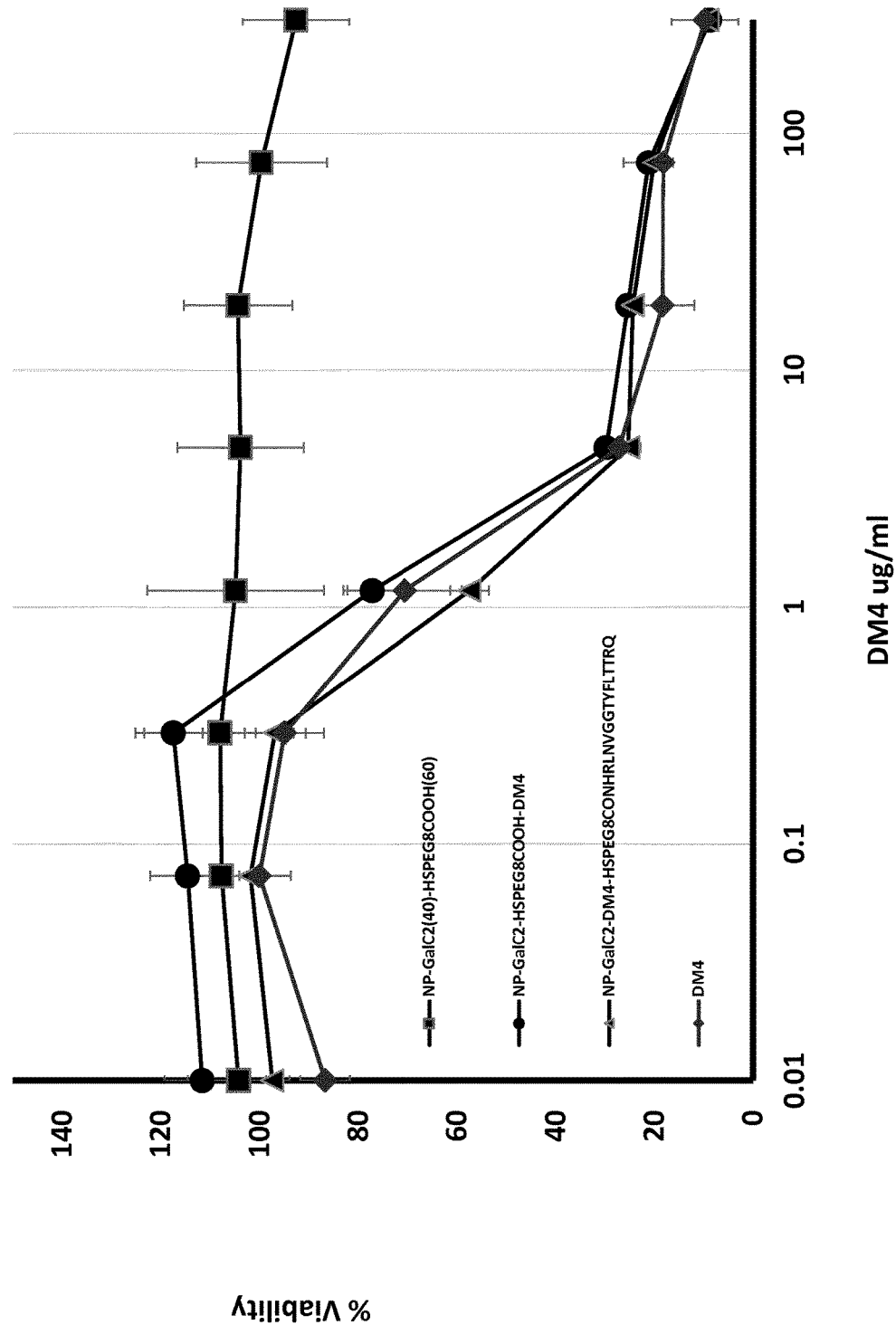
FIG. 9 shows the effect of various GNP constructs, and of free maytansinoid DM4, on cell viability on HEPG2 cells following 72 hours treatment at the indicated concentrations. Cell viability measured as percentage control in an MTT assay is plotted against concentration (of DM4 where present) in µg/ml (note the log scale of the x-axis). GNPs with a corona of galactose-C2 and HSPEG8COOH ligands (40:60 ratio) are shown with squares. This GNP, lacking DM4, exhibits essentially no toxicity under the conditions tested. GNPs with a corona of galactose-C2, HSPEG8COOH and DM4 ligands are shown with circles. The dose-toxicity curve closely resembles that of free DM4 shown with diamonds. GNPs with a corona of galactose-C2, HSPEG8COOH and DM4 ligands, wherein a proportion of the HSPEG8COOH ligands are conjugated to the N-terminus of the glypican-3-binding peptide RLNVGGTYFLT-TRQ (SEQ ID NO: 1)—approx. <1 peptide per nanoparticle—are shown with triangles. The dose-toxicity curve for these DM4 and glypican-3-binding peptide-loaded GNPs closely resembles that of free DM4 shown with diamonds.

The effect of the various GNP constructs, and of free maytansinoid DM4, on cell viability on HEPG2 cells following 72 hours treatment is shown in FIG. 9. Cell viability measured as percentage control in an MTT assay is plotted against concentration. The GNP lacking DM4 exhibited essentially no toxicity under the conditions tested. Both the GNPs with DM4 exhibited dose-toxicity curves that closely resembled that of free DM4. Taken together with the HCC targeting demonstrated by the GNPs having glypican-3-binding peptide as liver targeting agents (see Example 5), these results indicate that GNPs having a mixed corona of a dilution ligand, a glypican-3-binding peptide, and a chemotherapeutic such as maytansinoid DM4 is expected to demonstrate selected liver cancer cell killing while minimising off-target effects (i.e. minimising toxicity against healthy cells).

Example 7

Investigating Solubility of DM1-Loaded α-Galactose PEGylated Carboxyl Linker and DM1-Loaded α-Galactose Nanoparticles The aim of this experiment was to investigate the solubility on DM1 loaded α-Galactose PEGylated carboxyl linker and just DM1 loaded α-Galactose nanoparticles.

The following nanoparticles were constructed:
[α-Galactose] [DM$_1$] AuGNP:

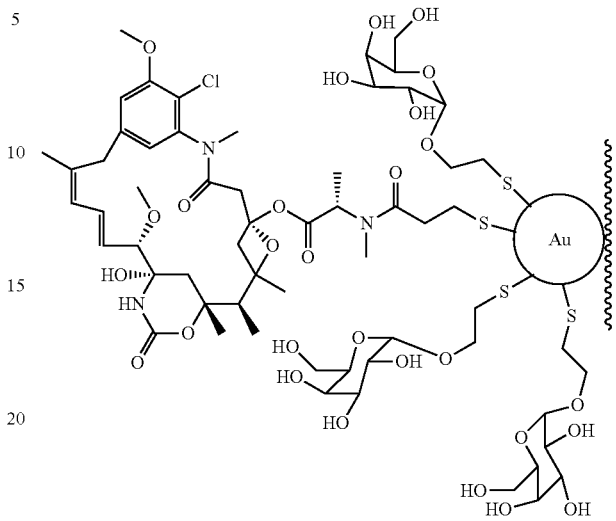

[α-Galactose] [Peg$_8$] [DM$_1$] AuGNP:

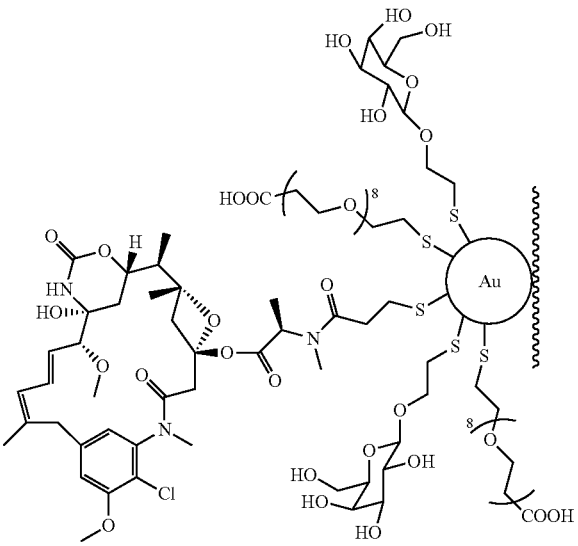

Procedure

The synthesis was carried out using ligand exchange method.

The nanoparticles were analysed by gold colorimetric assay, UV-Vis spectra, DLS and HPLC. HPLC was used to quantify any free DM$_1$ on the particle could affect the solubility or size distribution.

| ANALYSIS | | | | |
|---|---|---|---|---|
| Sample | [Au] (ppm) | UV-Vis | Free DM$_1$ | Ratio (DM$_1$/NP) |
| [α-Galactose] [DM$_1$] AuGNP | 865 | No | No | 4 |
| [α-Galactose] [Peg8] [DM1] AuGNP | 2100 | No | No | 4 |

DLS Analysis

[α-Galactose] [DM$_1$] AuGNP. [Au]: 150 ppm

Solvent: PBS×10.

Conclusions

[α-Galactose] [DM$_1$] AuGNP

In water, the [α-Galactose] [DM1] AuGNP nanoparticles exhibit excellent solubility and the size distribution is small (~4.00 nm) as expected.

In PBS, samples of the [α-Galactose] [DM1] AuGNP nanoparticles began to exhibit precipitation over time (24 hours), indicating less than optimal solubility.

[α-Galactose] [Peg$_8$] [DM$_1$] AuGNP

DM$_1$ loaded α-Galactose PEGylated gold nanoparticles were found to be completely soluble in both water and PBS, both analysis show small distribution.

Example 8

Investigating In Vitro and In Vivo Activity and Tolerability of [DM1]-[C2-α-Galactose]-[PEG$_8$COOH]@Au Nanoparticles

Figure 14:
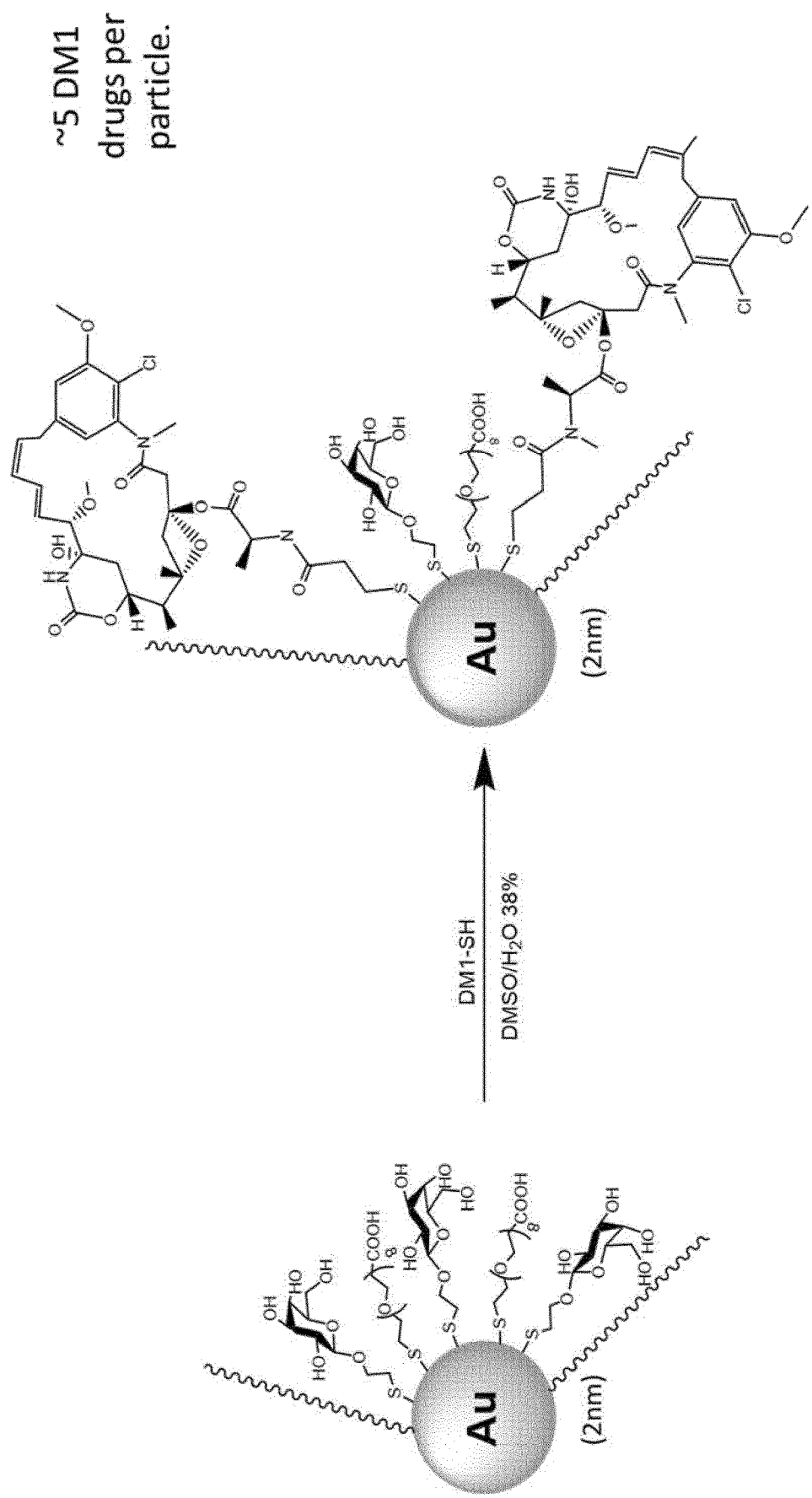
FIG. 14 shows a schematic overview of MTC-100038 synthesis. The left-hand nanoparticle has a gold core coronated with C2-alpha-galactose and $PEG_8COOH$ ligands. The nanoparticles are reacted with DM1 in $DMSO/H_2O$ to yield the MTC-100038 nanoparticles loaded with DMA (approx. 5 DM1 molecules per nanoparticle core), C2-alpha-galactose and $PEG_8COOH$ ligands (right-hand nanoparticle).

[DM1]-[C2-α-Galactose]-[PEG$_8$COOH]@Au gold nanoparticles were prepared by ligand exchange as described in Example 7 and depicted schematically in FIG. 14. The [DM1]-[C2-α-Galactose]-[PEG$_8$COOH]@Au gold nanoparticles were found to have an average DM1 loading of approximately 5 DM1 molecules per nanoparticle core. Hereafter, the [DM1]-[C2-α-Galactose]-[PEG$_8$COOH]@Au gold nanoparticle is referred to as "MTC-100038" or "MTC100038".

Figure 10:
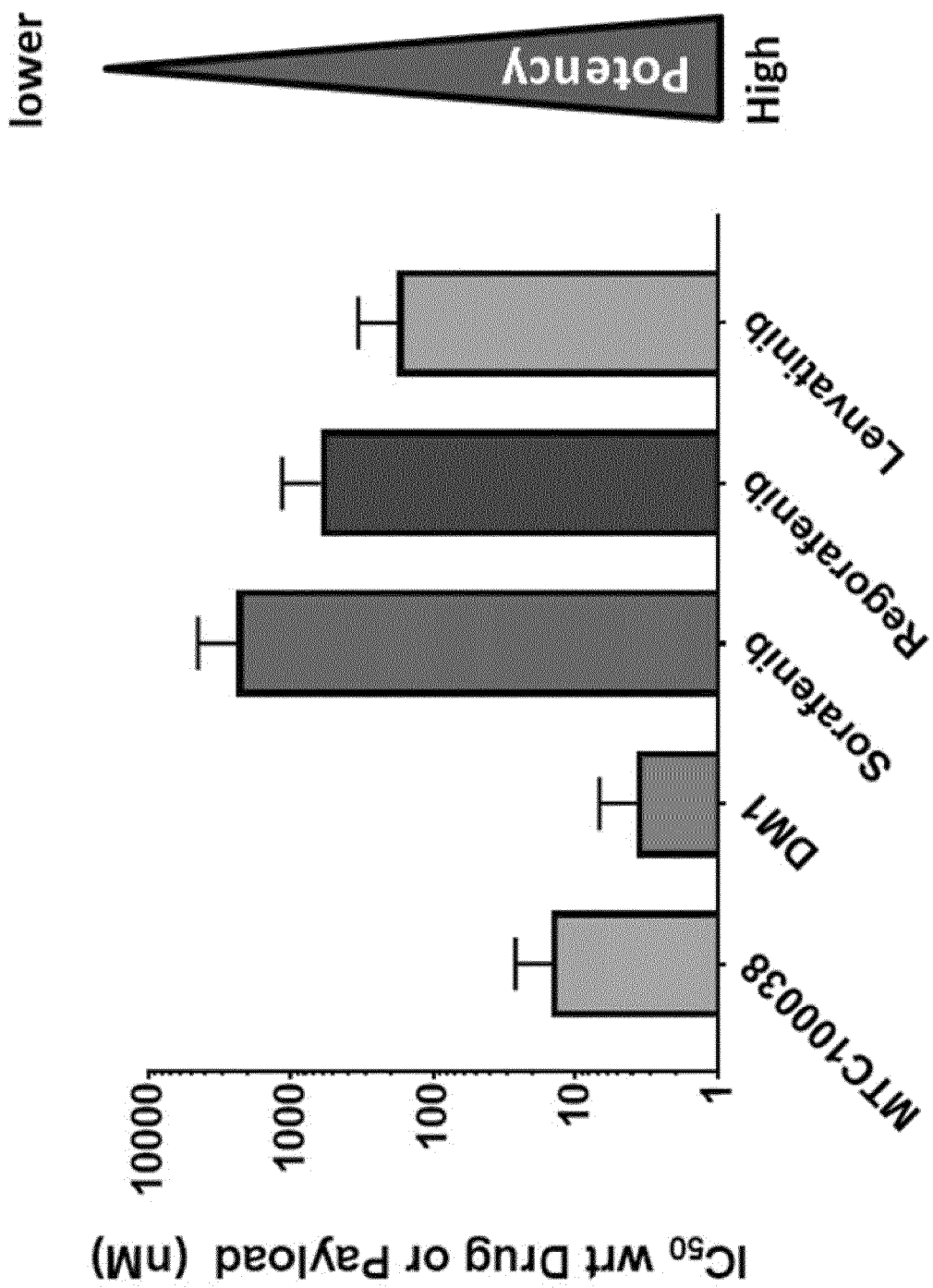
FIG. 10 shows a plot of results of in vitro cytotoxicity testing on Hep3B cells. The y-axis shows $IC_{50}$ for in nM (log scale) and the bars along the x-axis show the values±SEM for each of the drugs or constructs (left-to-right): MTC-100038, DM1, Sorafenib, Regorafenib, and Lenvatinib. A lower bar height indicates higher cytotoxic potency.

The cytotoxicity of gold nanoparticle constructs GalC2-PEG8COOH-GNP (parent, non-functionalised gold nanoparticle (MTC-100011)), and MTC-100038 were compared to free DM1 drug in the HCC cell lines HEPG2 and HEP3B. Both DM1 free drug and MTC-100038 resulted in significant and comparable levels of cytotoxicity, with IC$_{50}$ of 4.15 nM and 9.40 nM, respectively. The base gold nanoparticle, MTC-100011, i.e. without DM1 attached, did not display cytotoxicity in this assay. Importantly, the conjugation of DM1 to form MTC-100038 does not significantly alter cytotoxicity of DM1 compared to the parental drug (see Table below and FIG. 10).

|  | Hep3B | BEL7404 |
| --- | --- | --- |
| DM1 | 11 nM | 9 nM |
| MTC-100038 | 36 nM | 11 nM |

MTC-100038 was found to be a potent inhibitor of cell viability in the nM range over all (eight) human patient-derived cell lines tested. IC$_{50}$ values were comparable to those of free DM1, and cell viability at maximum inhibition was inhibited to a greater extent by MTC-100038 than free DM1 at equivalent DM1 concentration.

Following determination of in vitro cytotoxicity activity, in vivo testing was carried out, using both subcutaneous, and orthotopic xenograft mouse models, and implantation of recognised HCC cell lines where in vitro cytotoxicity had been confirmed. In all studies, tolerability was assessed pre-study to guide dose selection for the efficacy studies.

The effects of MTC-100038 on tumour growth in vivo have been studied in the following models:

Anti-tumour efficacy in subcutaneous model HEP3B xenograft model

Anti-tumour efficacy in subcutaneous BEL7404 xenograft model

Anti-tumour efficacy in orthotopic (left liver lobe) HEP3B xenograft model.

Figure 11:
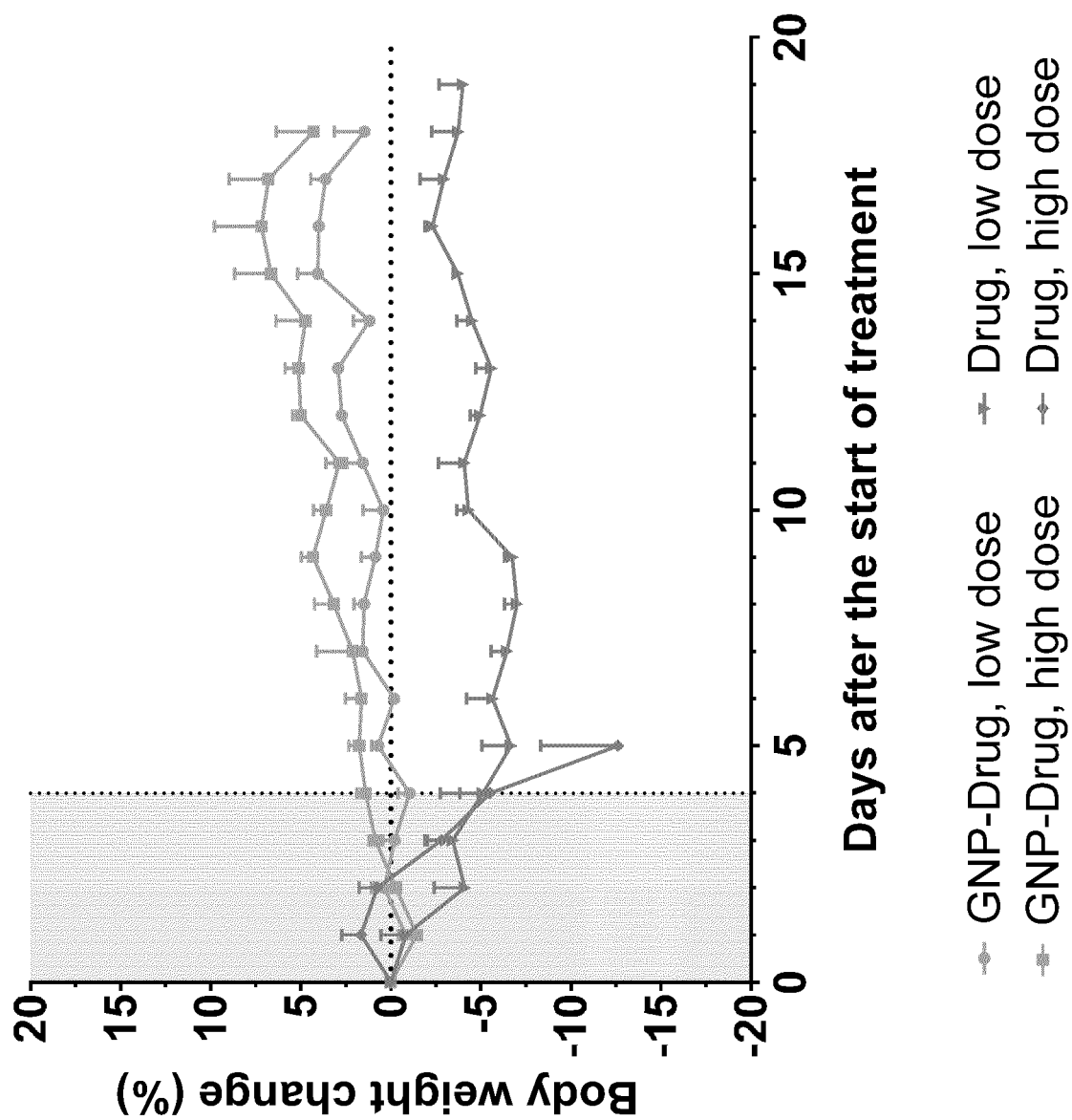
FIG. 11 shows a plot of body weight change (%) for animals by treatment group against time in days after start of treatment. The animals in this case were a mouse model with a human HCC xenograft. Animals dosed intravenously (I.V.) for five consecutive days (shaded area left of dotted vertical line) at either a low dose of 0.15 mg/kg of DM1 alone (inverted triangles) or high dose of 0.45 mg/kg DM1 alone (diamonds) or MTC-100038 at equivalent DM1 doses low (circles) and high (squares). Percentage body weight change was calculated based on animal weight on the first day of dosing. Data points represent percent group mean change in body weight±SEM. Body weight change is positive in the MTC-100038 nanoparticle-treated animals, but negative (low dose) or fatal (high dose) in the free DM1-treated animals.
Figure 12:
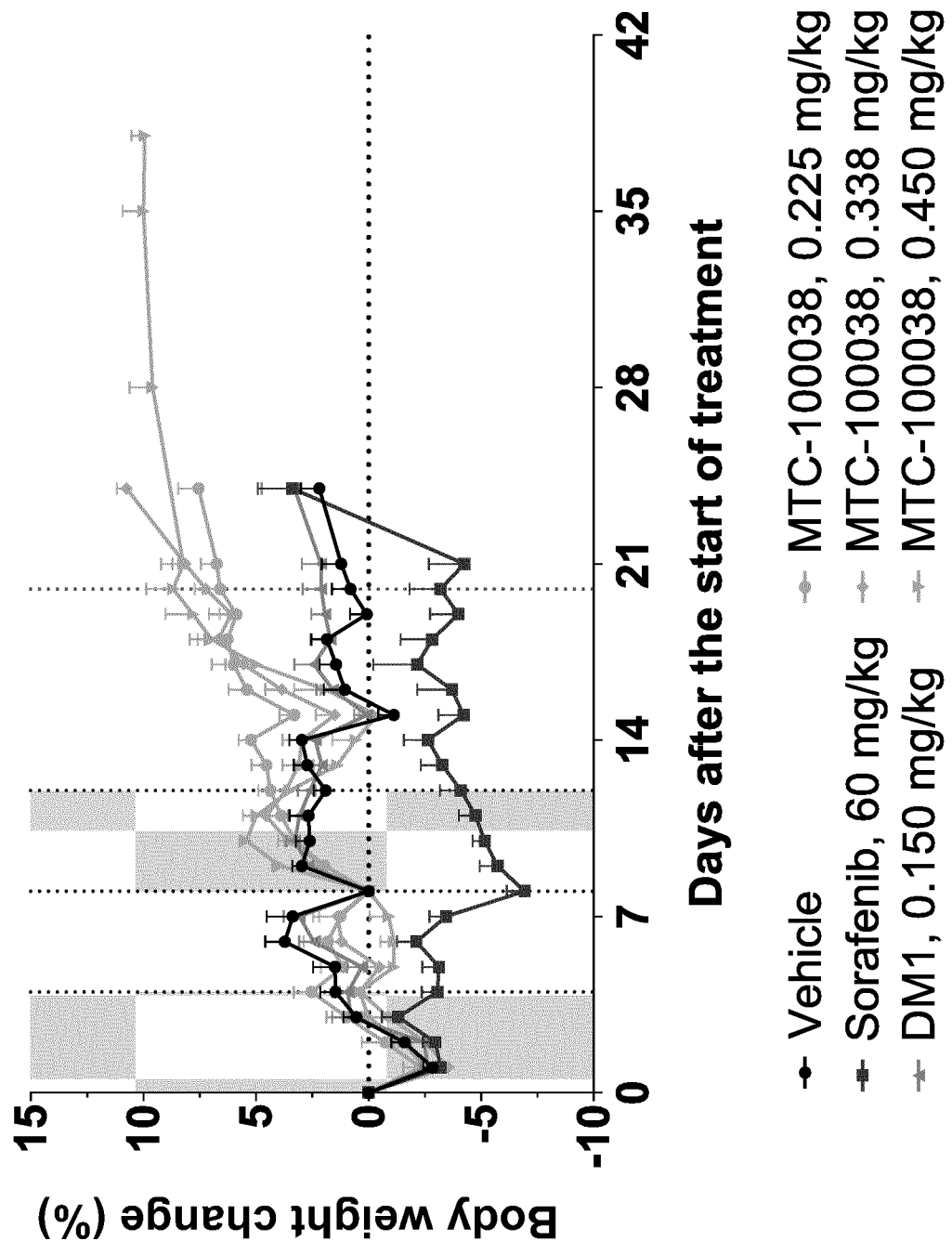
FIG. 12 shows a plot of body weight change (%) for animals by treatment group against time in days after start of treatment. The animals in this case were a mouse HCC model with a Hep3B orthotopic xenograft. MTC-100038, DM1, or vehicle were administered I.V. to BALB/c nude mice in 2×5 day cycles (shaded), whilst Sorafenib was administered by daily oral administration for 21 days (dashed line) at a dose of 60 mg/kg, which was the highest tolerated dose in this model. Percentage body weight change was calculated based on animal weight on the first day of dosing. Data points represent percent group mean change in body weight±SEM. Treatment groups were: Vehicle (black circles), Sorafenib 60 mg/kg (squares), free DM1 0.150 mg/kg (triangles), MTC-100038 0.225 mg/kg (green circles), MTC-100038 0.338 mg/kg (diamonds) and MTC-100038 0.450 mg/kg (inverted triangles). MTC-100038 was found to be well-tolerated with positive body weight change for all MTC-100038 concentrations tested which was well above that of the other treatment groups.

As shown in FIG. 11, MTC-100038 displayed improved tolerability relative to an otherwise lethal dose of DM1 (i.e. without nanoparticle delivery) in mouse model with human HCC xenograft. Moreover, FIG. 12 shows that MTC-100038 is well-tolerated compared to maximum tolerable dose (MTD) of Sorafenib in HEP3B orthotopic xenograft model of HCC.

Figure 13:
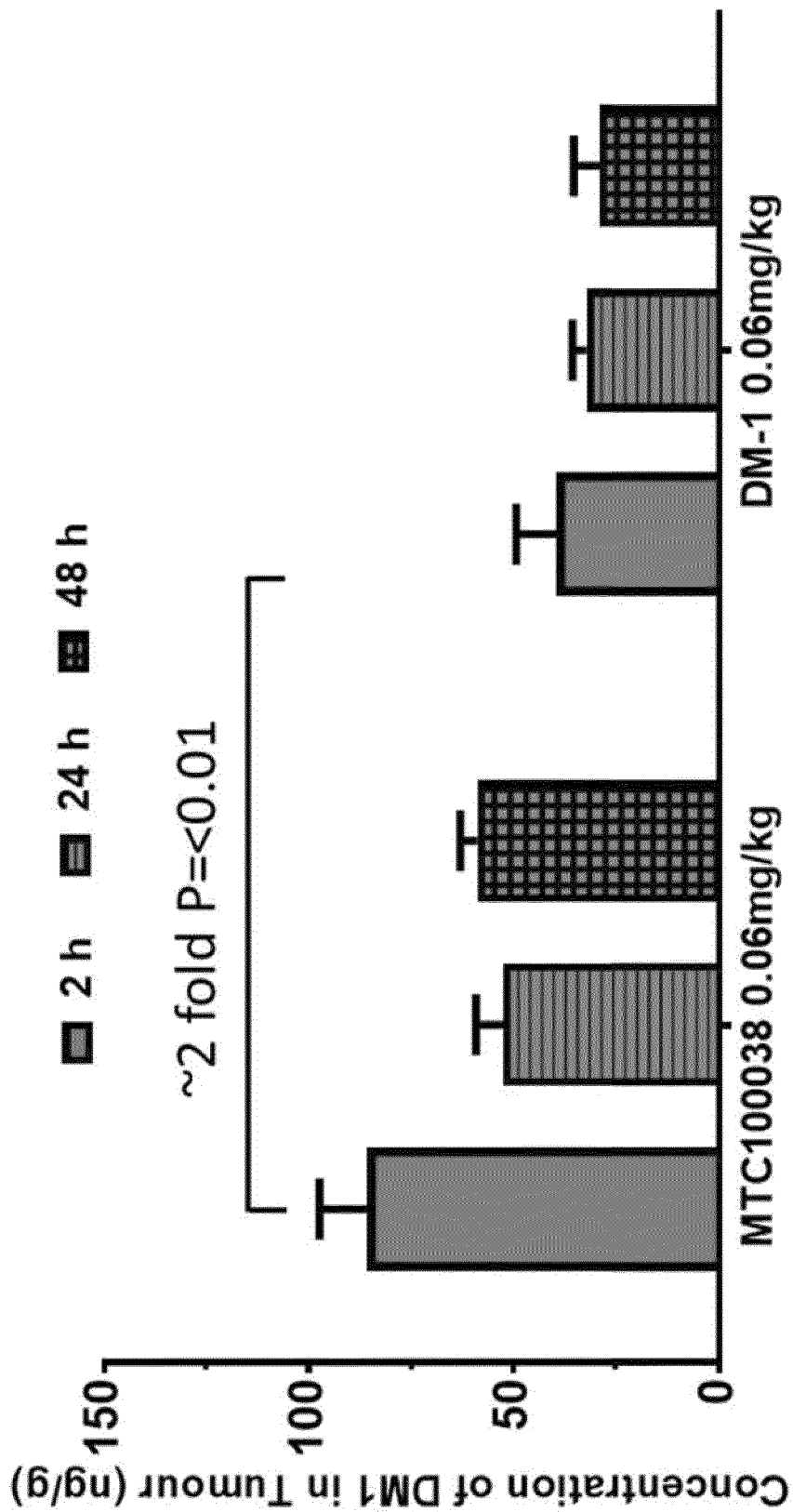
FIG. 13 shows a plot of tumour DM1 concentration (ng/g) for a subcutaneous Hep3B human hepatocellular cancer xenograft NOD/SCID mouse model. DM1 tumour concentration (mean±SEM) is shown for MTC-100038-treated (equivalent DM1 dose 0.06 mg/kg) animals (left-hand bars) and free DM1-treated animals (also 0.06 mg/kg dose) (right-hand bars). Time points are 2 hours (solid fill), 24 hours (horizontal lines) and 48 hours (checked pattern). A comparison of DM1 concentration at 2 hours shows that MTC-100038 nanoparticles exhibited around 2-fold higher concentration ($p<0.01$) than free DM1 treatment, indicating that nanoparticle delivery of DM1 using a nanoparticle construct of the present invention increased tumour uptake of DM1.

Furthermore, biodistribution studies have shown that MTC-100038 increases tumour DM1 delivery vs DM1 alone (FIG. 13).

The in vivo pharmacokinetics and biodistribution of DM1 was studied in the subcutaneous Hep3B human hepatocellular cancer xenograft model (Table 1). The concentration of gold and DM1 in liver and kidney samples was evaluated 2, 24 and 48 hours after the last drug administration.

DM1 concentration was highest in liver and kidney at 2 hours and thereafter progressively declined at 24 and 48 hours with an approximate tissue half-life of 12-24 hours. In the subcutaneous Hep3B tumour, DM1 concentration declined by about 40% between 2 and 24 hours after the last dose, but did not decline further at 48 hours. Importantly, the concentration of DM1 in the tumour after dosing with MTC-100038 was approximately twice that measured after the same dose of DM1 administered alone, indicating that the nanoparticle increased the uptake of DM1 (see FIG. 13).

Anti-Tumour Efficacy in Subcutaneous HEP3B Xenograft Model

The in vivo anti-tumour efficacy of MTC-100038 in a subcutaneous Hep3B hepatocellular cancer xenograft model in NOD/SCID mice was evaluated. Briefly NOD/SCID mice (18-22 g, n=10 per group) were implanted subcutaneously with HEP 3B hepatocellular cells (3×10$^6$) in 0.1 mL PBS for tumour development. Group/dosing assignment commenced when tumours reached a pre-determined volume of ~200 mm$^3$ subcutaneous tumours (n=10 per group). Dosing (i.v.) commenced on a QD×5 (daily for 5 days) basis for MTC-100038 and free DM1 at the concentrations indicated in the table below. Tumour size was measured twice weekly, and the volume was expressed in mm$^3$. The tumour size was then used for calculations of T/C values. The T/C value (in percent) is an indication of anti-tumour effectiveness (optimally, a test article is considered to have anti-tumour activity when T/C is 50% or less); T and C are the mean volumes of the treated and control groups, respectively, on a given day.

As shown in the following table MTC-100038 slows tumour growth in a sub-cutaneous Hep3B human xenograft in NOD/SCID (immuno-compromised) mice in a dose-dependent fashion.

| Treatment | Tumour size (mm$^3$)* | T/C** |
| --- | --- | --- |
| Vehicle | 1427 ± 221 | — |
| DM1 0.1125 mg/kg | 1217 ± 254 | 78.9 |
| MTC-100038 0.122 mg/kg | 1363 ± 225 | 95.5 |
| MTC-100038 0.225 mg/kg | 1029 ± 160 | 72.1 |
| MTC-100038 0.45 mg/kg | 221 ± 29 | 15.5 |

*Measurements taken on day 13. Data = Mean ± SEM
**T/C is a measure of tumour growth inhibition. It is calculated by dividing the average tumour volume for the treatment group, by the average volume for the vehicle group. Optimally, an effective treatment exhibits T/C ≤ 50%.

The above data indicate that MTC-100038 has higher anti-tumour activity than the parental drug DM1, providing a complete block on tumour growth from the point of treatment at a dose of 0.45 mg/kg. The enhanced efficacy of MTC-100038 reflects a higher DM1 concentration in tumour tissue which, without wishing to be bound by any particular theory, was believed to be due to at least:
a) enhanced uptake of DM1 into the cancer cells when it was administered on the nanoparticle, and
b) the altered biodistribution and lower toxicity of MTC-100038, which enabled 3 times higher doses of DM1 to be administered to the mice compared to DM1 alone Anti-Tumour Efficacy in Subcutaneous BEL7404 Xenograft Model The in vivo anti-tumour efficacy of MTC-100038 in a subcutaneous BEL7404 hepatocellular cancer xenograft model in NOD/SCID mice was evaluated. Briefly NOD/SCID mice (18-22 g, n=10 per group) were implanted subcutaneously with BEL7404 tumour cells ($3\times10^6$) in 0.1 ml of PBS for tumour development. Group/dosing assignment commenced when tumours reached a pre-determined volume of ~200 mm$^3$ subcutaneous tumours. Treatment groups and dosing are as indicated in the table below.

Tumour size was measured twice weekly, and the volume was expressed in mm$^3$. The tumour size was then used for calculations of T/C values. The results of the tumour growth inhibition analysis are shown in the table below.

| Treatment | Dosing Route/Schedule | Tumour size (mm$^3$)* | T/C** |
|---|---|---|---|
| Vehicle (PBS) | i.v./QD × 5 (D0-4) + QD × 5 (D8-12) | 2347 ± 191 | — |
| Sorafenib 60 mg/kg | p.o./QD × 21 | 984 ± 64 | 41.9 |
| DM1 0.15 mg/kg | i.v./QD × 5 (D0-4) + QD × 5 (D8-12) | 2656 ± 180 | 113.2 |
| MTC-100038 0.225 mg/kg | i.v./QD × 5 (D0-4) + QD × 5 (D8-12) | 1295 ± 70 | 55.2 |
| MTC-100038 0.375 mg/kg | i.v./QD × 5 (D0-4) + QD × 5 (D8-12) | 154 ± 35 | 6.6 |

*Measurements taken on day 13. Data = Mean ± SEM
**T/C is a measure of tumour growth inhibition. It is calculated by dividing the average tumour volume for the treatment group, by the average volume for the vehicle group. Optimally, an effective treatment exhibits T/C ≤ 50%.

The above data show that treatment with DM1 alone at dose level of 0.15 mg/kg produced no anti-tumour activity, compared to the vehicle control group. Treatment with Sorafenib at 60 mg/kg over 21 days resulted in significant tumour growth inhibition, compared to vehicle. MTC-100038 showed dose-dependent inhibition of tumour growth, with a dose level of 0.3375 mg/kg producing superior anti-tumour activity, compared to Sorafenib.

Anti-Tumour Efficacy in Orthotopic HEP3B Xenograft Model

The in vivo anti-tumour efficacy of MTC-100038 in an orthotopic hepatocellular cancer xenograft model in BALB/c nude mice was evaluated. Briefly, female BALB/c nude mice (18-23 g, n=10/group), were implanted with approximately $3\times10^6$ Hep3B-Luc cells mixed with BD Matrigel in 20 μL (PBS:Matrigel=1:1). Animals were selected and randomized (based on their bioluminescence density) on day 7 after tumour implantation to 6 groups using randomized block design based upon their bioluminescence. The treatment and dosing schedule was as shown in the table below.

The tumour bioluminescence was used for the calculation of T/C value (in percent), where T and C are the mean bioluminescence of the treated and control groups, respectively, on a given day. Statistical analysis of difference in bioluminescence among the groups and the analysis of drug interaction were conducted on the data obtained at the best therapeutic time point after the final dose (the 21st day after the start of treatment).

A one-way ANOVA was performed to compare bioluminescence among groups, and when a significant F-statistics (a ratio of treatment variance to the error variance) was obtained, comparisons between groups were carried out with Games-Howell test with p<0.05 statistically significant.

The results of the tumour growth inhibition analysis calculated on bioluminescence measurements at day 21 are shown in the table below.

| Treatment | Dosing route/schedule | Bioluminescence (photons/s)* | T/C (%)** |
|---|---|---|---|
| Vehicle (PBS) | i.v./QD × 5 (D0-4) + QD × 5 (D8-12) | 1.45E+10 ± 3.02E+09 | |
| Sorafenib 60 mg/kg | p.o./QD × 21 | 3.24E+09 ± 7.73E+08 | 22.3 |
| DM1 0.15 mg/kg | i.v./QD × 5 (D0-4) + QD × 5 (D8-12) | 1.21E+10 ± 1.56E+09 | 83.4 |
| MTC-100038 0.225 mg/kg | i.v./QD × 5 (D0-4) + QD × 5 (D8-12) | 7.00E+09 ± 2.48E+09 | 48.3 |
| MTC-100038 0.375 mg/kg | i.v./QD × 5 (D0-4) + QD × 5 (D8-12) | 4.09E+09 ± 9.57E+08 | 28.2 |
| MTC-100038 0.45 mg/kg | i.v./QD × 5 (D0-4) + QD × 5 (D8-12) | 2.92E+08 ± 9.17E+07 | 2.0 |

*Measurements taken on day 21. Data = Mean ± SEM
**T/C is a measure of tumour growth inhibition. It is calculated by dividing the average bioluminescence for the treatment group, by the average bioluminescence for the vehicle group. Optimally, an effective treatment exhibits T/C ≤ 50%.

The above data show that the mean bioluminescence of vehicle treated control mice reached $1.45\times10^{10}$ (photons/second) on day 21 after the start of treatment. Treatment with sorafenib at a dose level of 60 mg/kg produced significant anti-tumour activity, the mean bioluminescence was $3.24\times10^9$ (photons/second) (T/C value=22.3%, p=0.046, compared with vehicle group). Treatment with DM1 at dose level of 0.15 mg/kg produced no anti-tumour activity compared with vehicle group). Treatment with MTC-100038 at dose level of 0.45 mg/kg produced significant anti-tumour activity, the mean bioluminescence was $2.92\times10^8$ (photons/second) (T/C value=2.0%, p=0.013, compared with vehicle group). Body weight change, as a surrogate marker of tolerability, suggests that over the range of doses used in this study, MTC-100038 was well-tolerated.

Summary

A [DM1]-[C2-α-Galactose]-[PEG8COOH]@Au nanoparticle according to the present invention, MTC-100038, has the potential to be of significant benefit in the treatment of hepatocellular carcinoma; a condition in which prognosis is poor and treatment options are limited. Currently available chemotherapies are limited by their inherent toxicities, tolerability, and lack of efficacy. Due to these limitations, chemotherapy has not met with much success for treating liver cancer.

In vivo and in-vitro efficacy data described above indicate that GNP bound DM1 in the construct MTC-100038 results in improved tolerability compared to DM1 alone, and provides the ability to deliver efficacious doses of DM1 in pre-clinical HCC models. This contrasts with the highest tolerated dose of DM1 alone which lacked efficacy in these same studies. This improved tolerability resulted in the ability to deliver up to 200% more DM1, when conjugated to the gold nanoparticles. Biodistribution measures as part of these studies also demonstrated a more favourable biodistribution of DM1 to diseased cancer cells in the liver rather than normal hepatocyte cells and other tissues. The antitumour activity of MTC-100038 was greater than the maximum tolerable dose (MTD) of the current standard of care (SoC), Sorafenib, in these same studies.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

5. The nanoparticle according to claim 1, wherein the core comprises at metal selected from the group consisting of: Au, Ag, Cu, Pt, Pd, Fe, Co, Gd, Zn or any combination thereof.

6. The nanoparticle according to claim 5, wherein the core comprises gold.

7. The nanoparticle according to claim 1, wherein the diameter of the core is in the range 1 nm to 5 nm.

8. The nanoparticle according to claim 1, wherein the diameter of the nanoparticle including its ligands is in the range 3 nm to 50 nm.

The invention claimed is:

1. A nanoparticle comprising:
   a core comprising a metal and/or a semiconductor; and
   a plurality of ligands covalently linked to the core, wherein said ligands comprise:
   (i) at least one galactose ligand;
   (ii) at least one maytansinoid DM1 ligand; and
   (iii) at least one dilution ligand comprising a poly or oligo ethylene glycol chain having a carboxylic acid end group.

2. The nanoparticle according to claim 1, wherein the at least one dilution ligand comprises SH-PEG-COOH.

3. The nanoparticle according to claim 1, wherein the at least one dilution ligand comprises:
   HS—(OCH$_2$CH$_2$)$_q$—COOH, where q is between 2 and 30, optionally between 6 and 10, or where q is between 20 and 60.

4. The nanoparticle according to claim 1, wherein the at least one dilution ligand comprises:

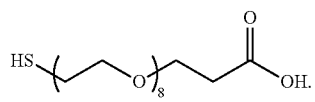

9. A nanoparticle having the following structure:

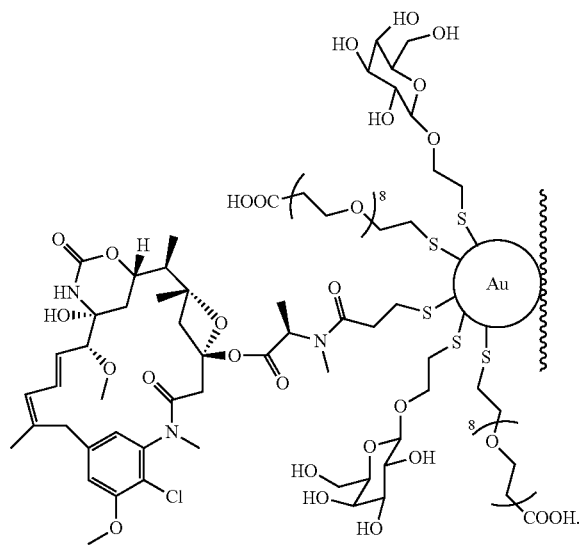

10. A pharmaceutical composition comprising a plurality of the nanoparticles of claim 1, and at least one pharmaceutically acceptable carrier or diluent.

11. The pharmaceutical composition according to claim 10, wherein the pharmaceutical composition is a sustained release formulation and wherein at least a portion of the plurality of nanoparticles are encapsulated in a biocompatible polymer.

12. The pharmaceutical composition according to claim 11, wherein the sustained release formulation is in the form of a microparticle, a microsphere, a bead or a film.

13. The pharmaceutical composition according to claim 10, wherein the composition is in injectable form.

14. A method of treating a liver disorder in a mammalian subject, comprising administering the nanoparticle according to claim 1 to a mammalian subject in need of therapy.

15. The method according to claim 14, wherein said liver disorder comprises a primary or secondary cancer of the liver.

16. The method according to claim 15, wherein said cancer is hepatocellular carcinoma (HCC).

17. The method according to claim 15, wherein said cancer is selected from: heptoblastoma, cholangiocarcinoma, cholangiocellular cystadenocarcinoma, angiosarcoma, hemangioendothelioma, embryonal sarcoma, fibrosarcoma, leiomyosarcoma and rhabdomyosarcoma.

18. The method according to claim 14, wherein said nanoparticle is administered concurrently, sequentially or separately with a second anti-cancer agent.

19. The method according to claim 18, wherein said second anti-cancer agent comprises a kinase inhibitor selected from the group consisting of: Sorafenib, Regorafenib and Lenvatinib.

20. An article of manufacture comprising:
a nanoparticle according to claim 1;
a container for housing the nanoparticle or pharmaceutical composition; and
an insert or label.

21. The article of manufacture according to claim 20, wherein the insert and/or label provides instructions, dosage and/or administration information relating to the use of the nanoparticle or pharmaceutical composition in the treatment of a liver disorder in a mammalian subject.

* * * * *